(12) United States Patent
Guldiken et al.

(10) Patent No.: US 9,821,310 B2
(45) Date of Patent: Nov. 21, 2017

(54) TWO-STAGE MICROFLUIDIC DEVICE FOR ACOUSTIC PARTICLE MANIPULATION AND METHODS OF SEPARATION

(75) Inventors: Rasim Oytun Guldiken, Tampa, FL (US); Myeong Chan Jo, Tampa, FL (US); Jiang Zhe, Akron, OH (US)

(73) Assignee: The University of Akron, Akron, OH (US)

( * ) Notice: Subject to any disclaimer, the term of this patent is extended or adjusted under 35 U.S.C. 154(b) by 980 days.

(21) Appl. No.: 14/007,483

(22) PCT Filed: Mar. 30, 2012

(86) PCT No.: PCT/US2012/031526
§ 371 (c)(1),
(2), (4) Date: Sep. 25, 2013

(87) PCT Pub. No.: WO2012/135663
PCT Pub. Date: Oct. 4, 2012

(65) Prior Publication Data
US 2014/0008307 A1    Jan. 9, 2014

Related U.S. Application Data

(60) Provisional application No. 61/470,124, filed on Mar. 31, 2011.

(51) Int. Cl.
| | |
|---|---|
| *G01N 1/18* | (2006.01) |
| *B01L 3/00* | (2006.01) |
| *G01N 33/50* | (2006.01) |
| *G01N 33/574* | (2006.01) |
| *G01N 15/14* | (2006.01) |

(52) U.S. Cl.
CPC .... *B01L 3/502761* (2013.01); *G01N 33/5005* (2013.01); *G01N 33/5044* (2013.01); *G01N 33/574* (2013.01); *B01L 2200/0636* (2013.01); *B01L 2200/0652* (2013.01); *B01L 2200/10* (2013.01); *B01L 2300/0816* (2013.01); *B01L 2300/0864* (2013.01); *B01L 2400/0436* (2013.01); *G01N 2015/142* (2013.01)

(58) Field of Classification Search
CPC ............. B01D 21/283; B01L 3/502753; B01L 3/502761; B01L 2400/0436; B01L 2200/0652; B01L 2300/0816; B01L 2200/0636; B01L 2200/10; B01L 2300/0864; G01N 33/5044; G01N 2015/142; G01N 33/5005; G01N 33/574
See application file for complete search history.

(56) References Cited

U.S. PATENT DOCUMENTS

| | | | | |
|---|---|---|---|---|
| H001568 | H * | 8/1996 | Huang | C02F 1/36 210/702 |
| 2010/0078384 | A1 * | 4/2010 | Yang | B01D 21/283 210/645 |
| 2010/0126922 | A1 * | 5/2010 | Takahashi | B01D 21/283 210/201 |

(Continued)

*Primary Examiner* — Walter D. Griffin
*Assistant Examiner* — Cameron J Allen
(74) *Attorney, Agent, or Firm* — Renner Kenner Grieve Bobak Taylor & Weber

(57) ABSTRACT

Exemplary embodiments of the present disclosure provide for two-stage microfluidic devices using surface acoustic waves, methods of use thereof, methods of making, methods of focusing and separating particles, and the like.

7 Claims, 24 Drawing Sheets

(56) References Cited

U.S. PATENT DOCUMENTS

2010/0139377 A1* 6/2010 Huang ............... G01N 15/1404
  73/61.75
2010/0193407 A1* 8/2010 Steinberg .......... B01L 3/502761
  209/155

* cited by examiner

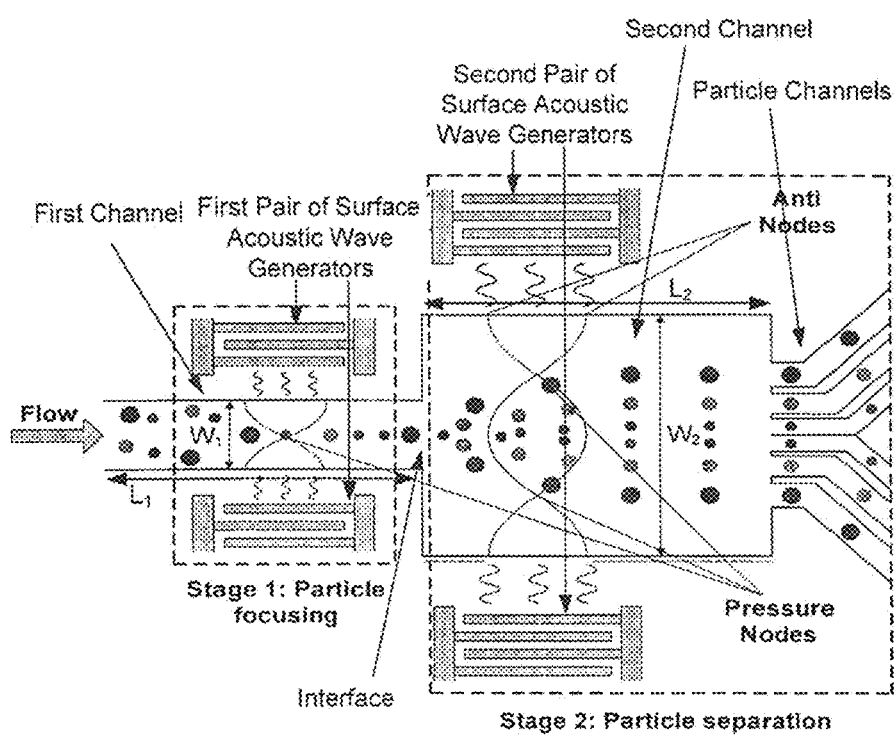
FIG. 1.1

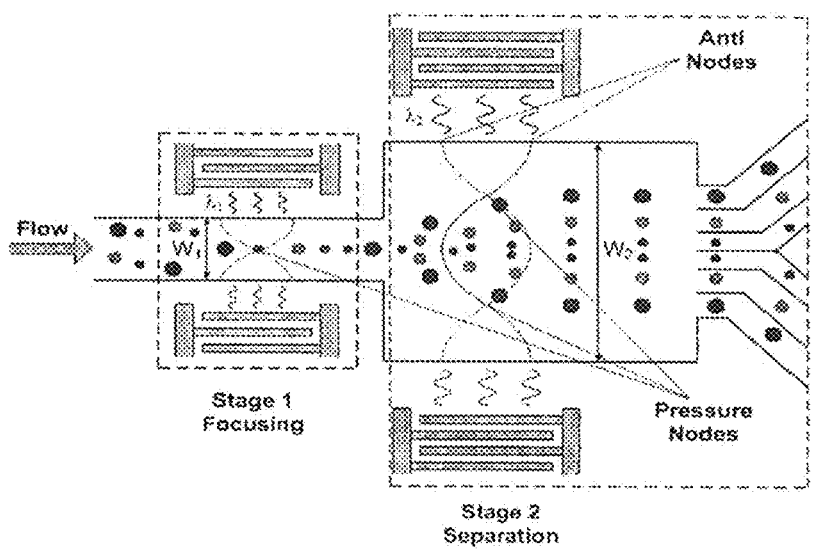
FIG. 2.1
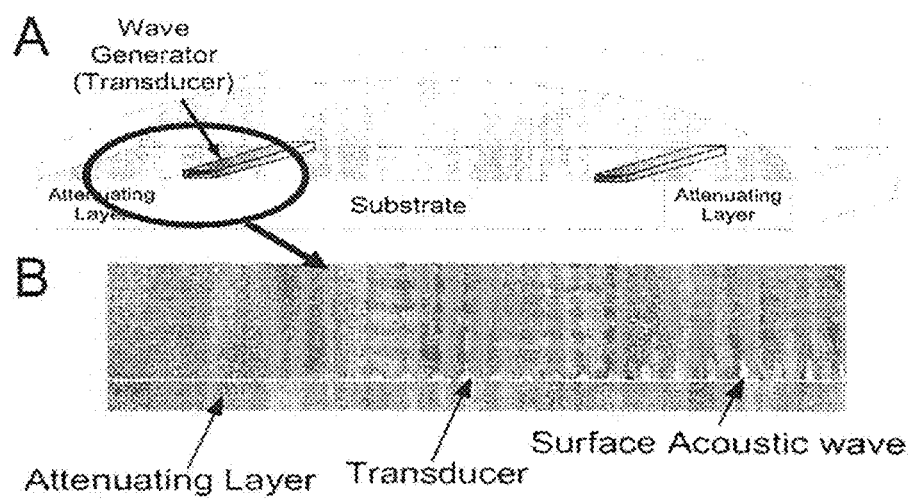
FIG. 2.2

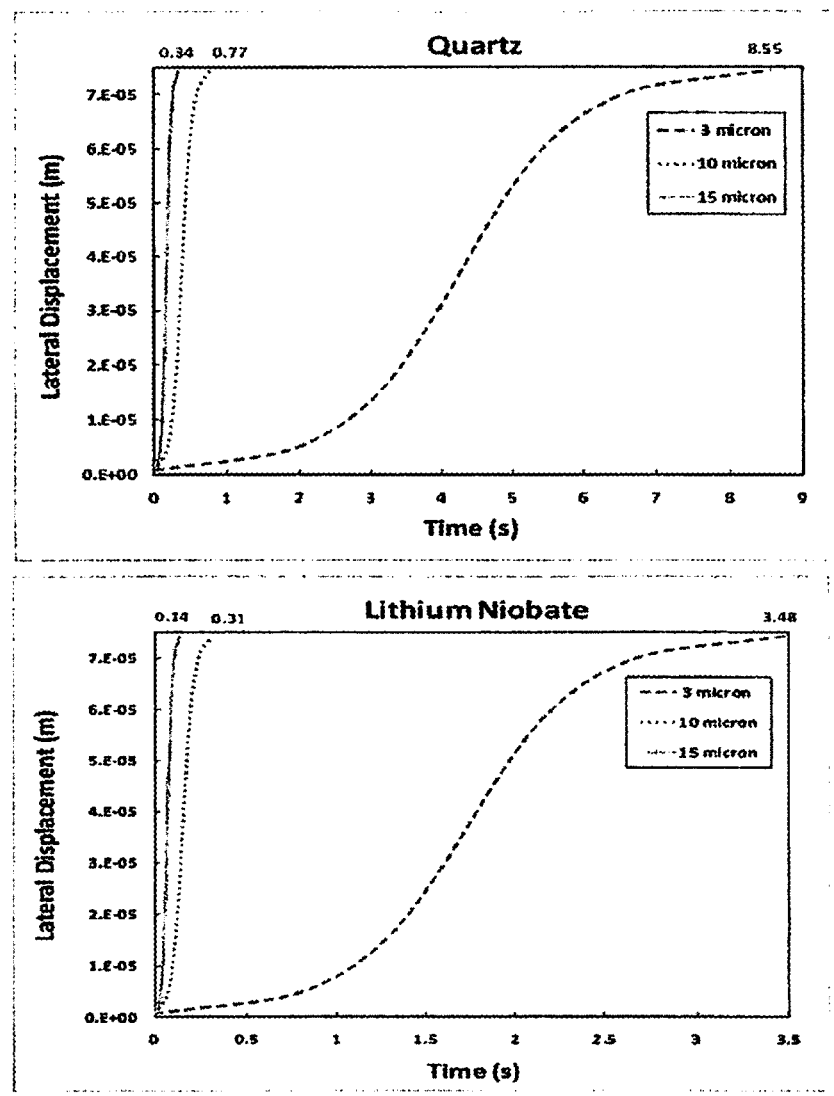
FIG. 2.3

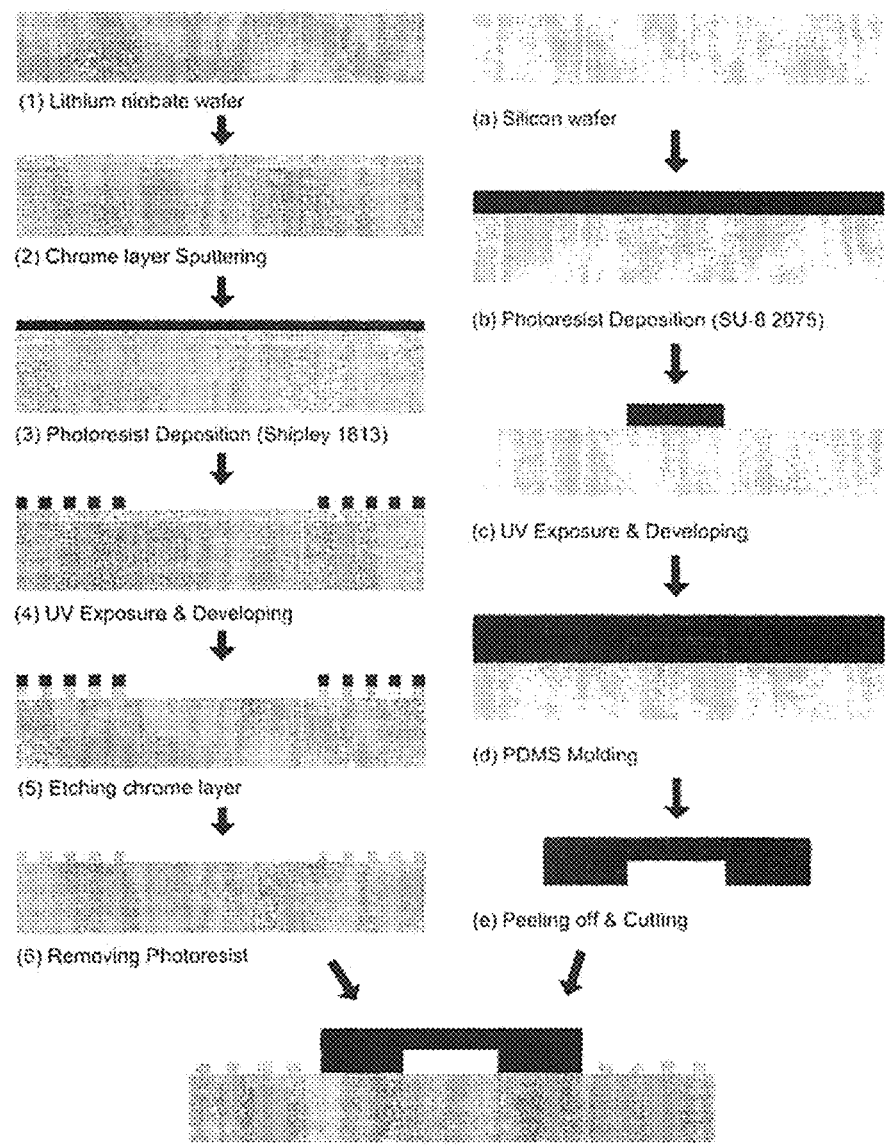
FIG. 2.4

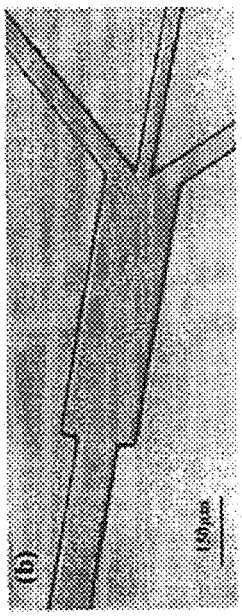
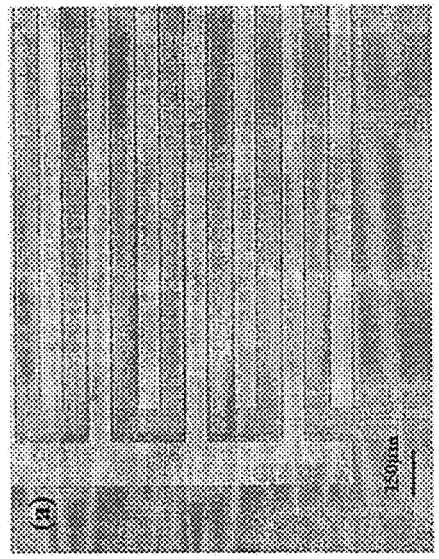
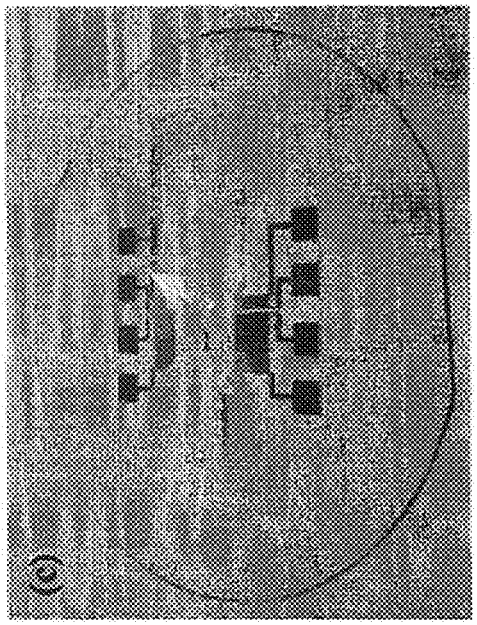
FIG. 2.5

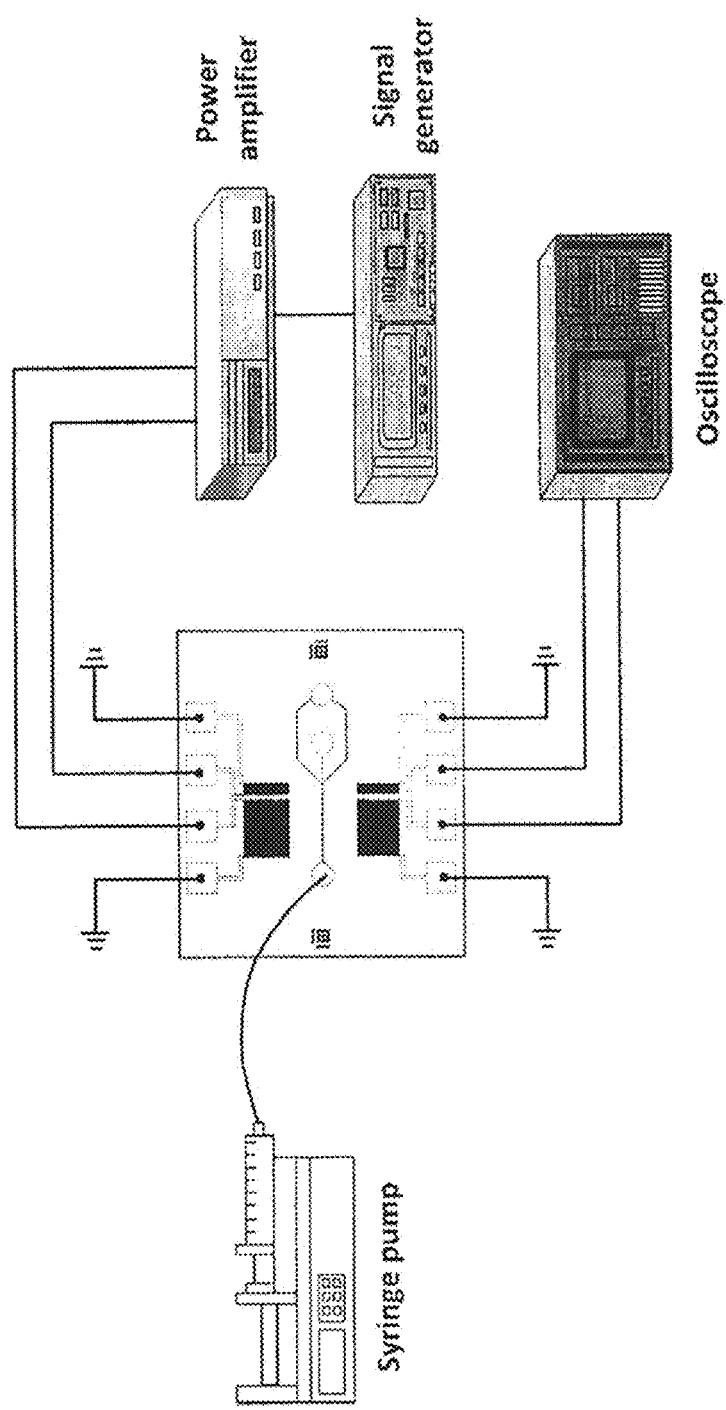
FIG. 2.6

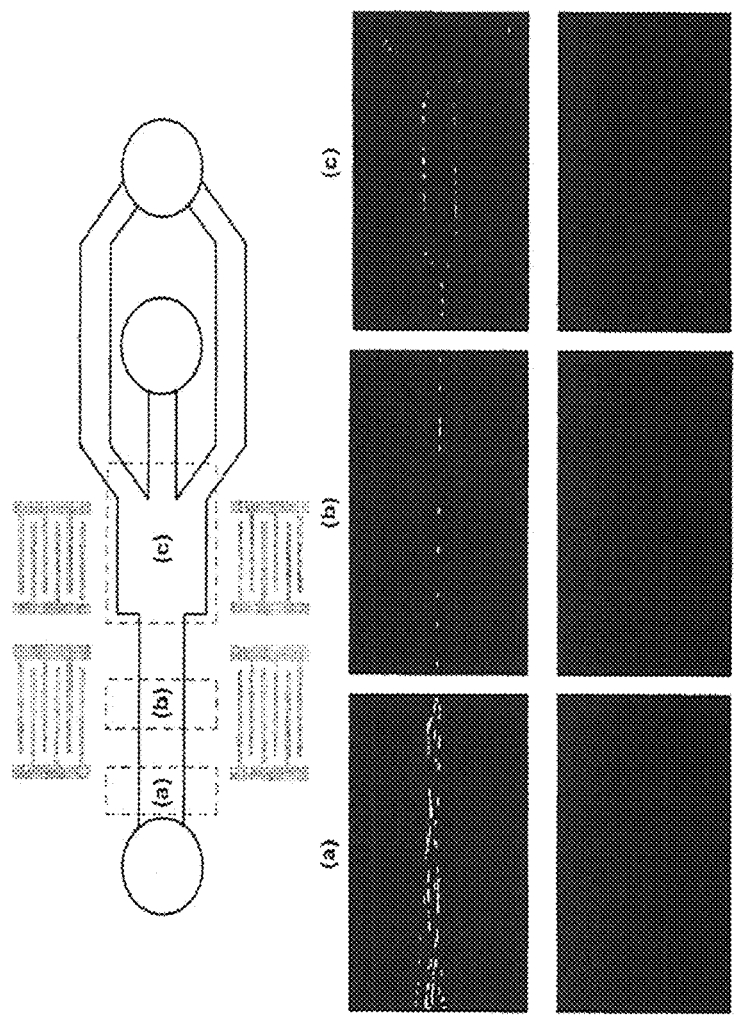
FIG. 2.7

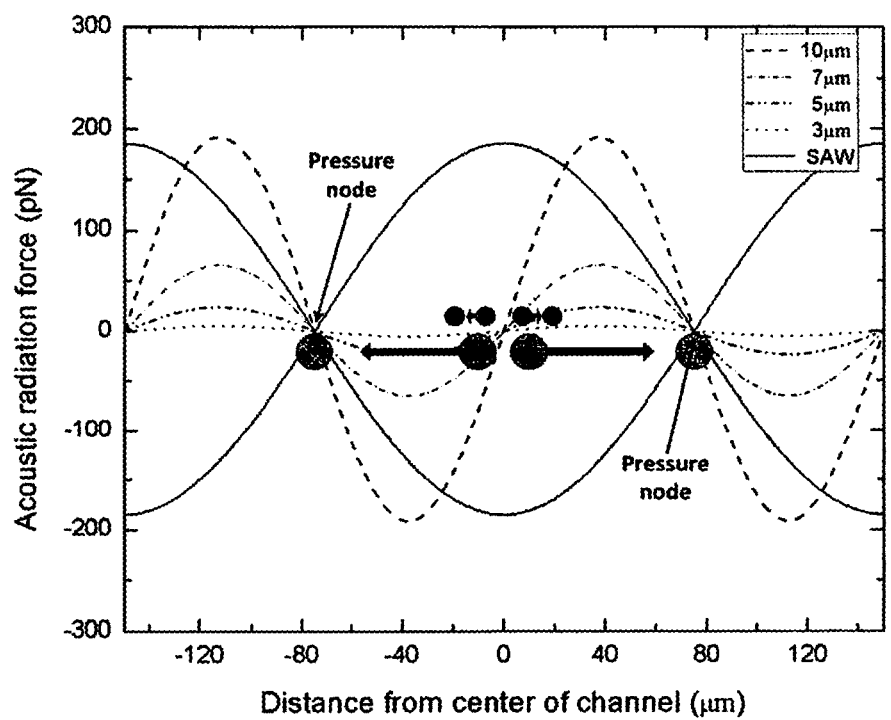
FIG. 3.1

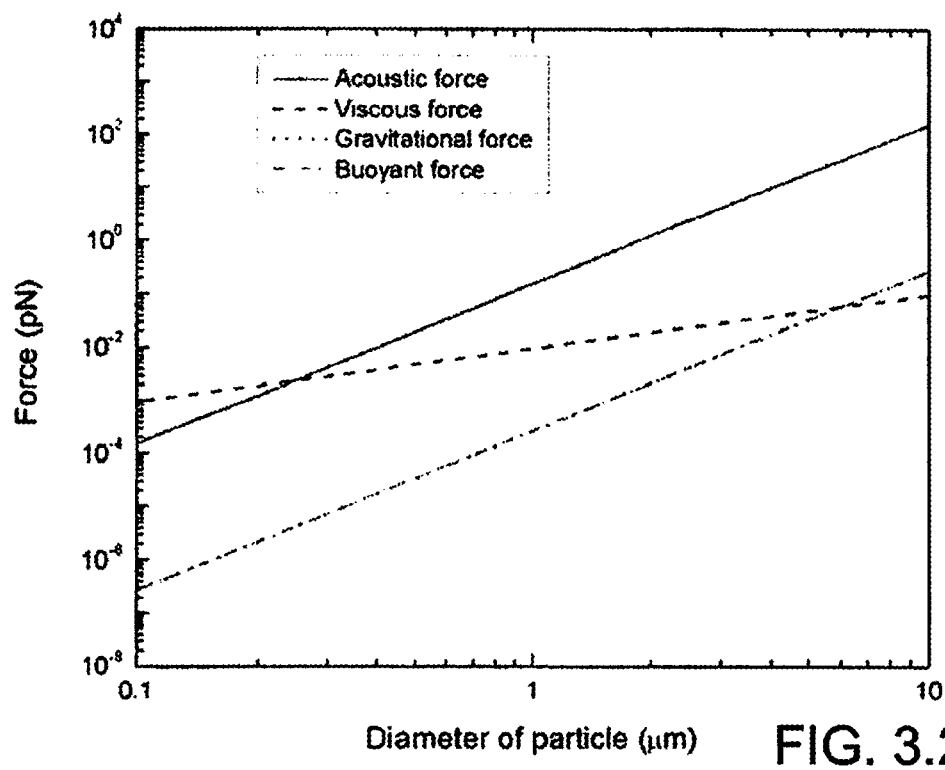
FIG. 3.2
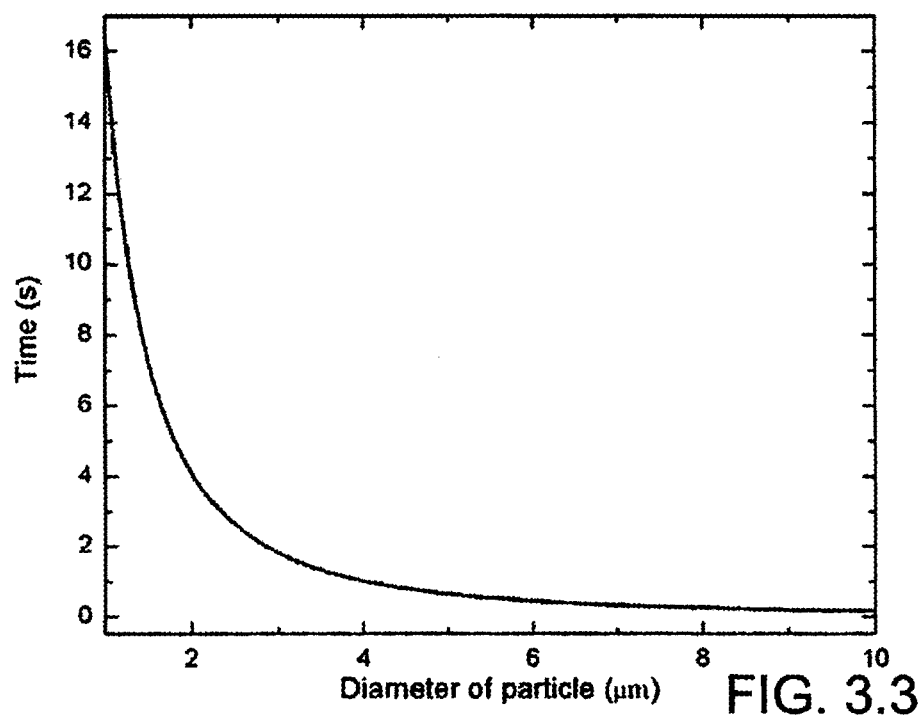
FIG. 3.3

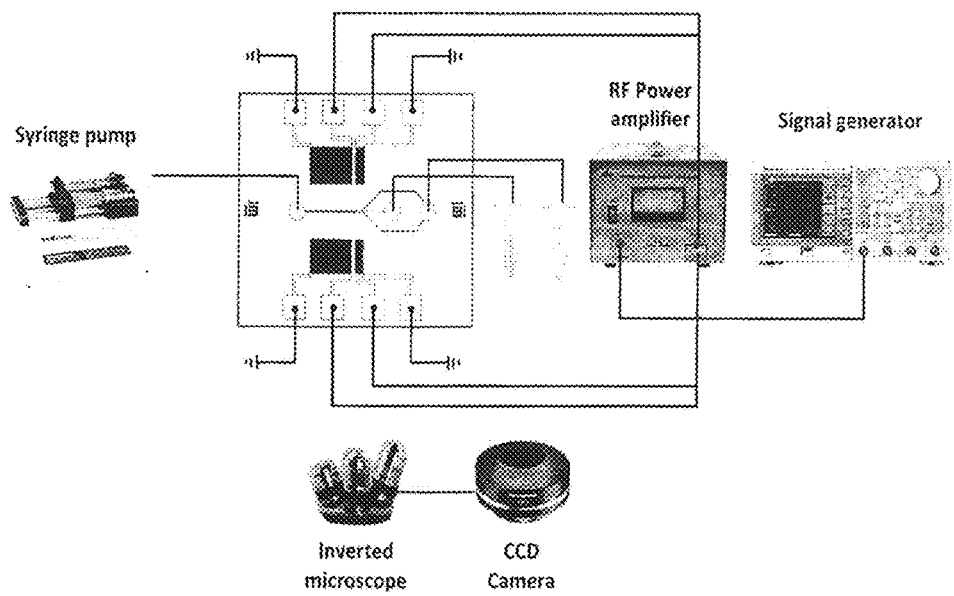
FIG. 3.4

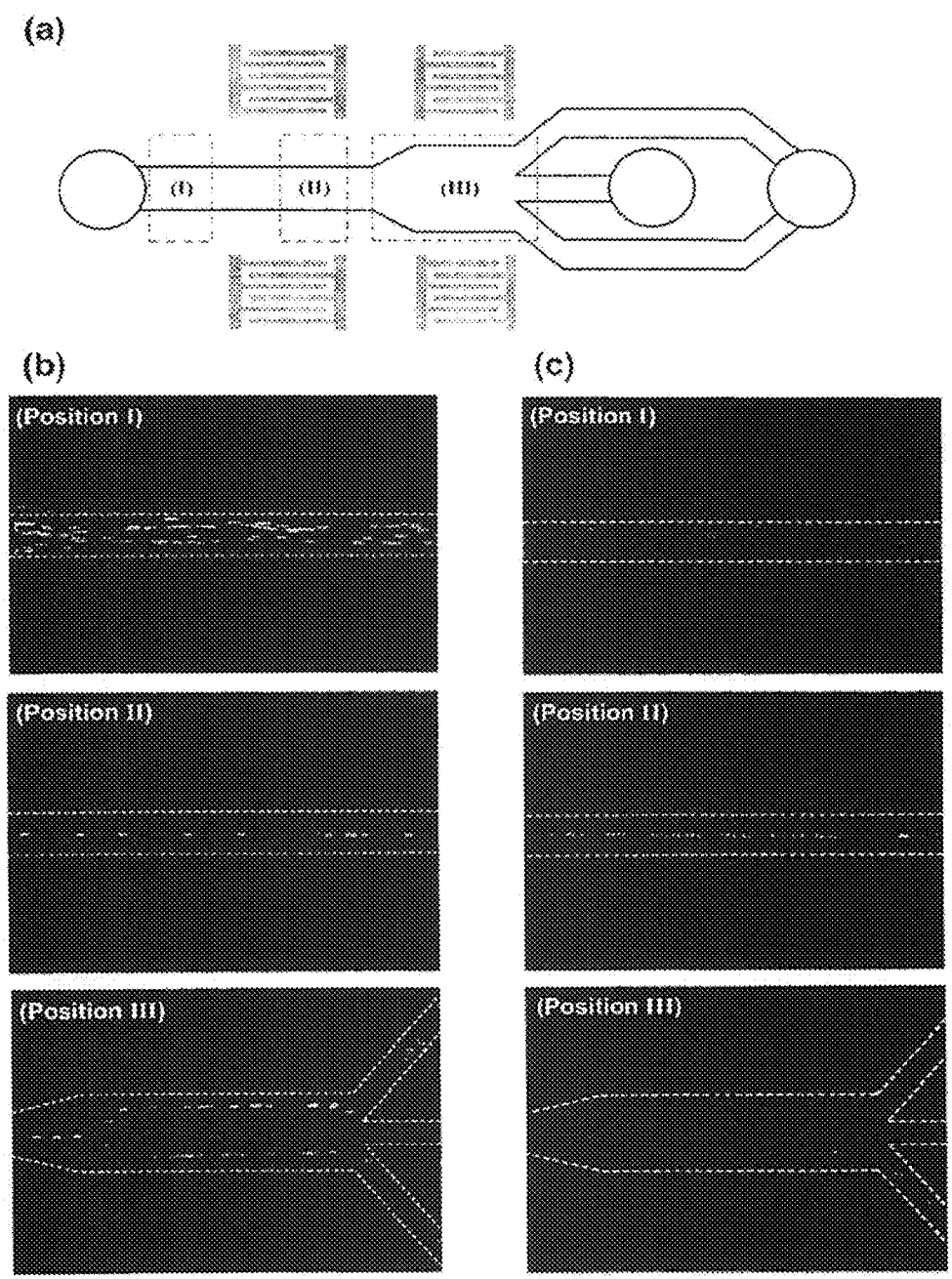
FIG. 3.5

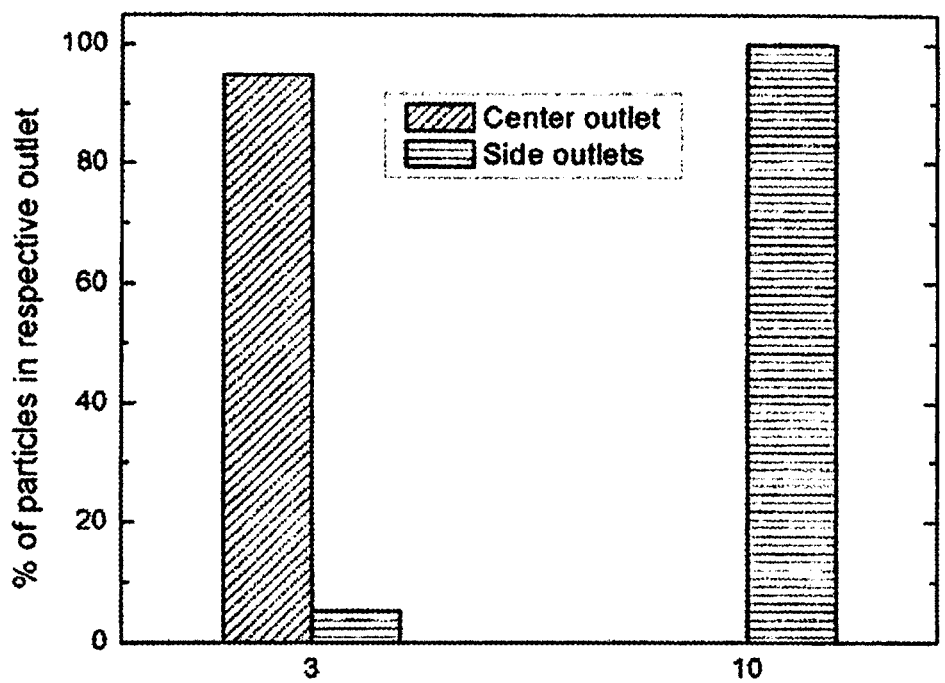
FIG. 3.6
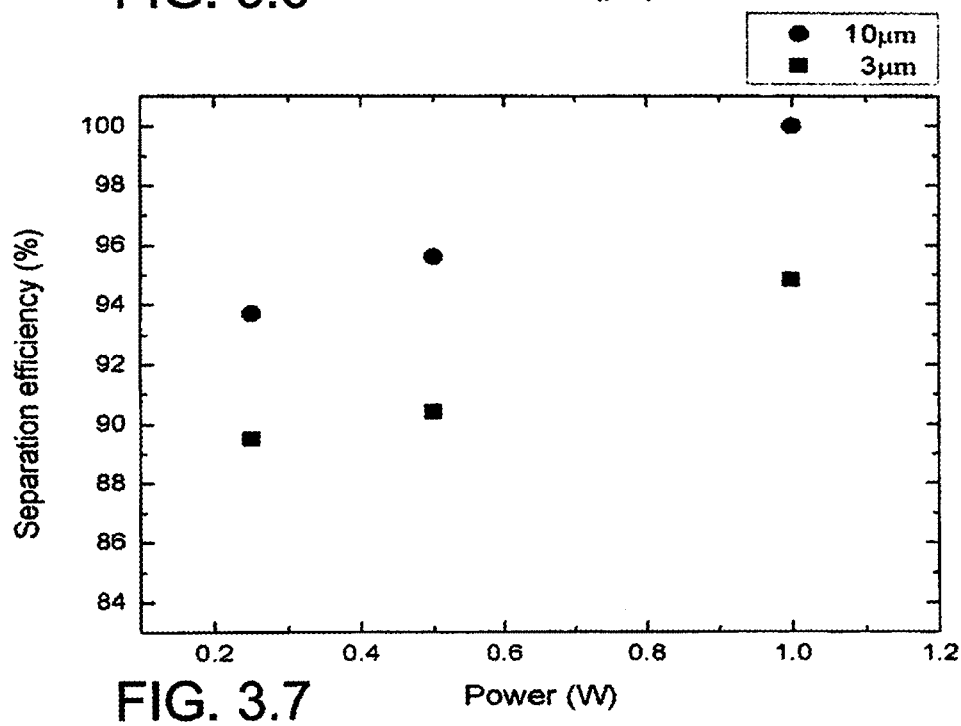
FIG. 3.7

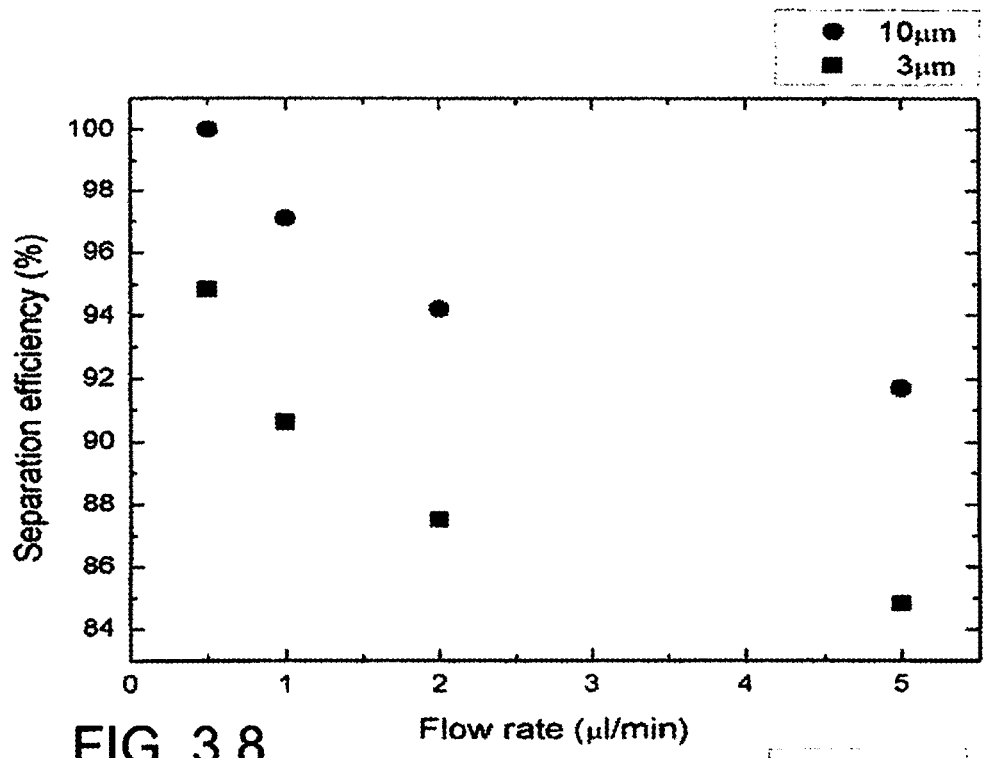
FIG. 3.8
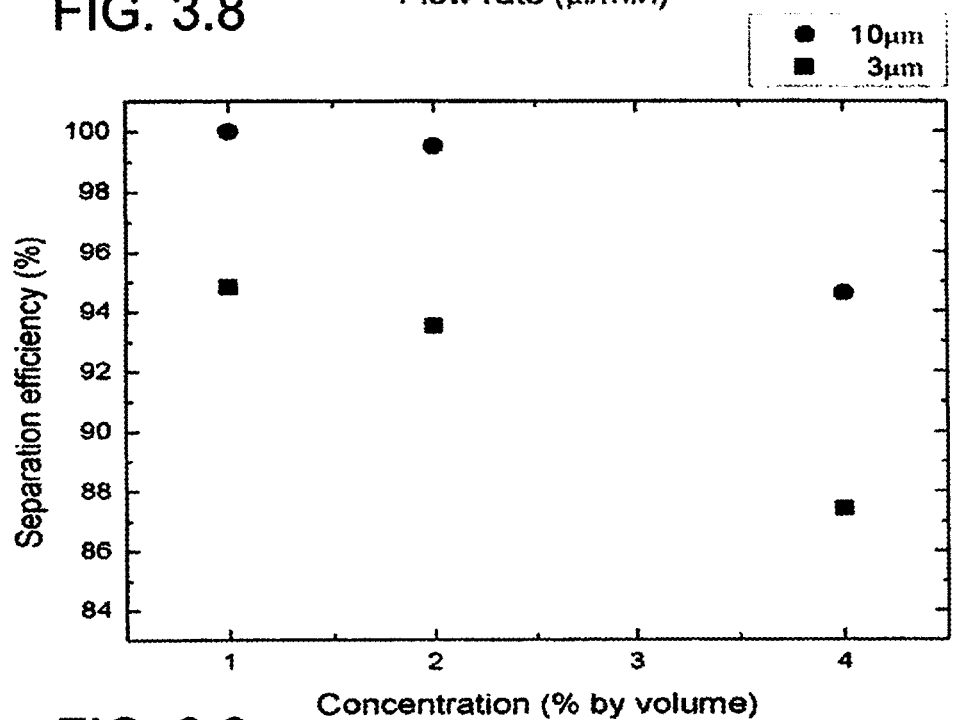
FIG. 3.9

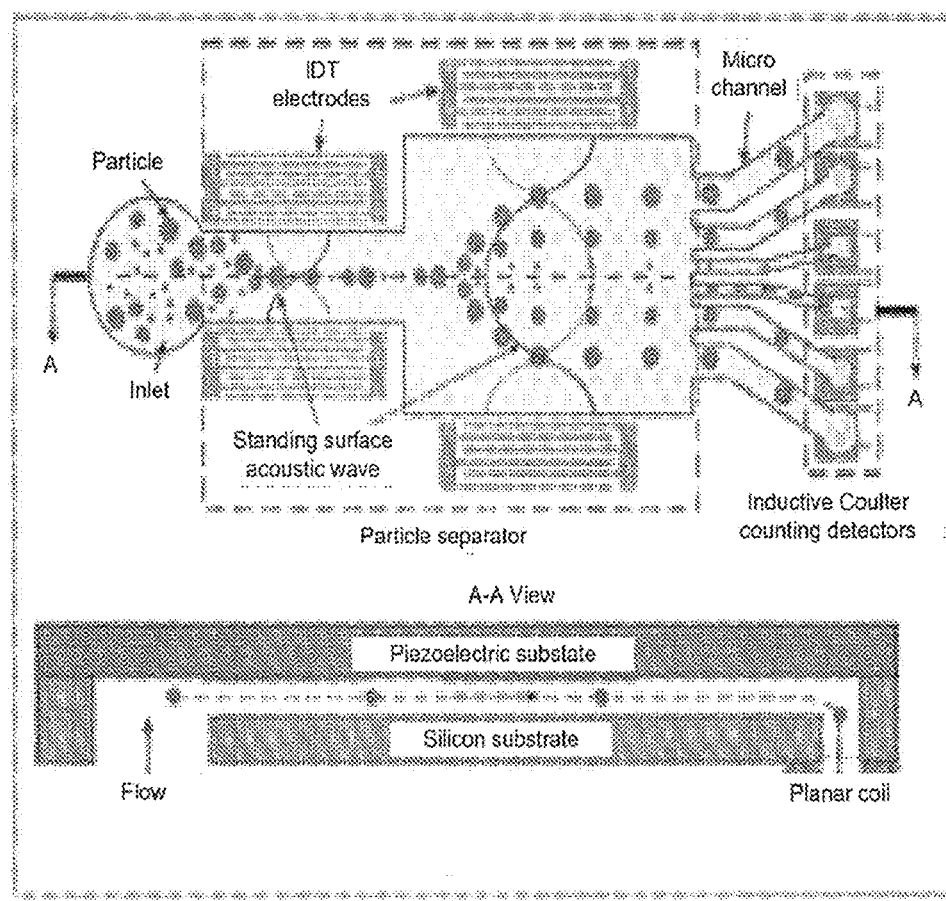
FIG. 4.1

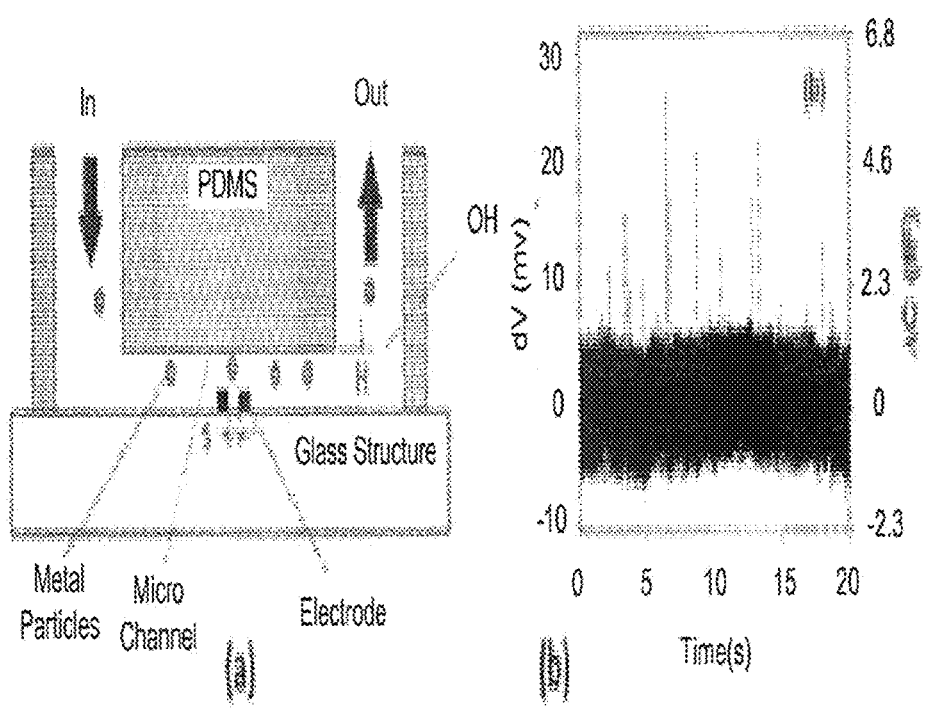
FIG. 4.2

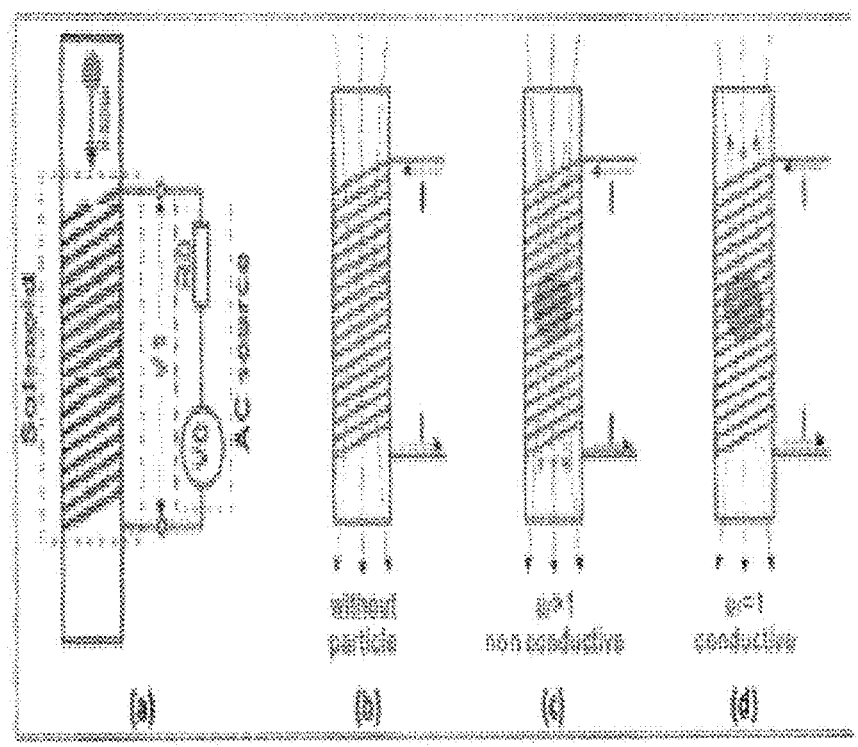
FIG. 4.3

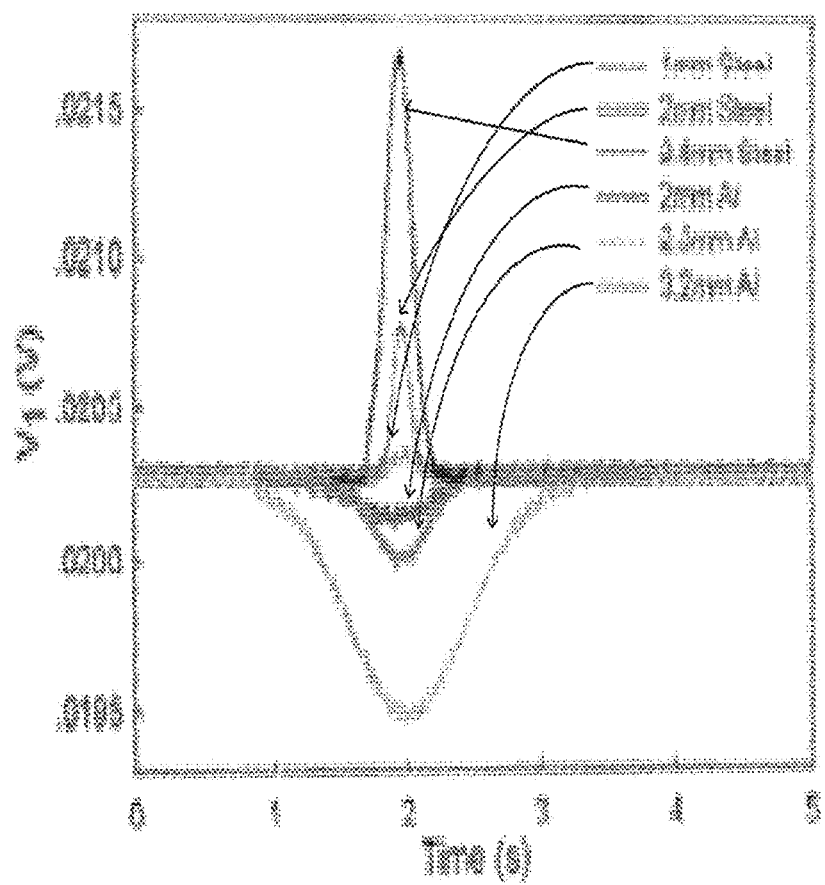
FIG. 4.4

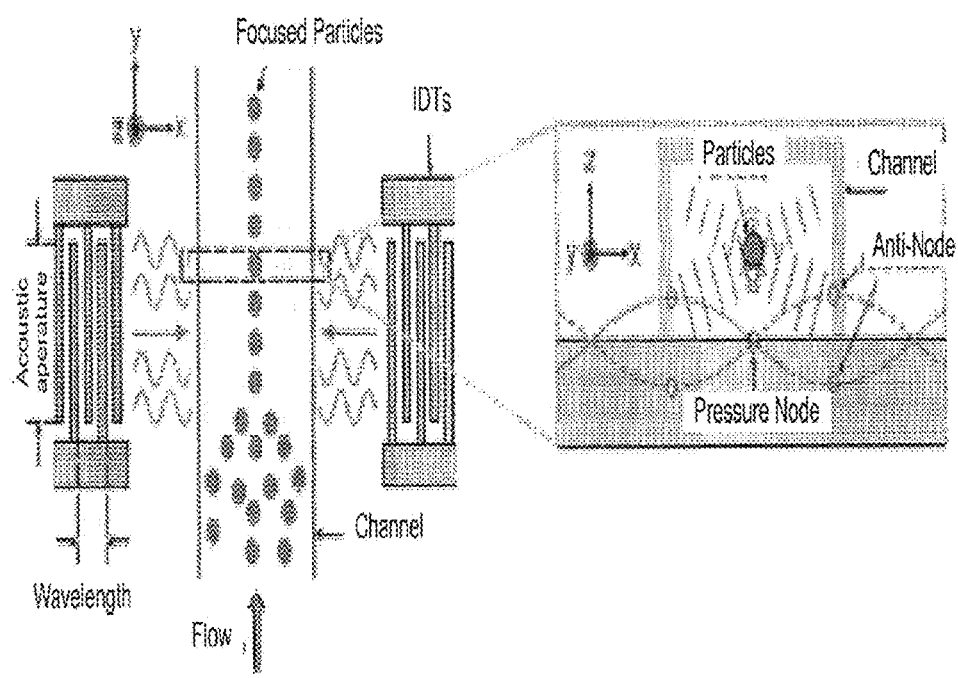
FIG. 4.5

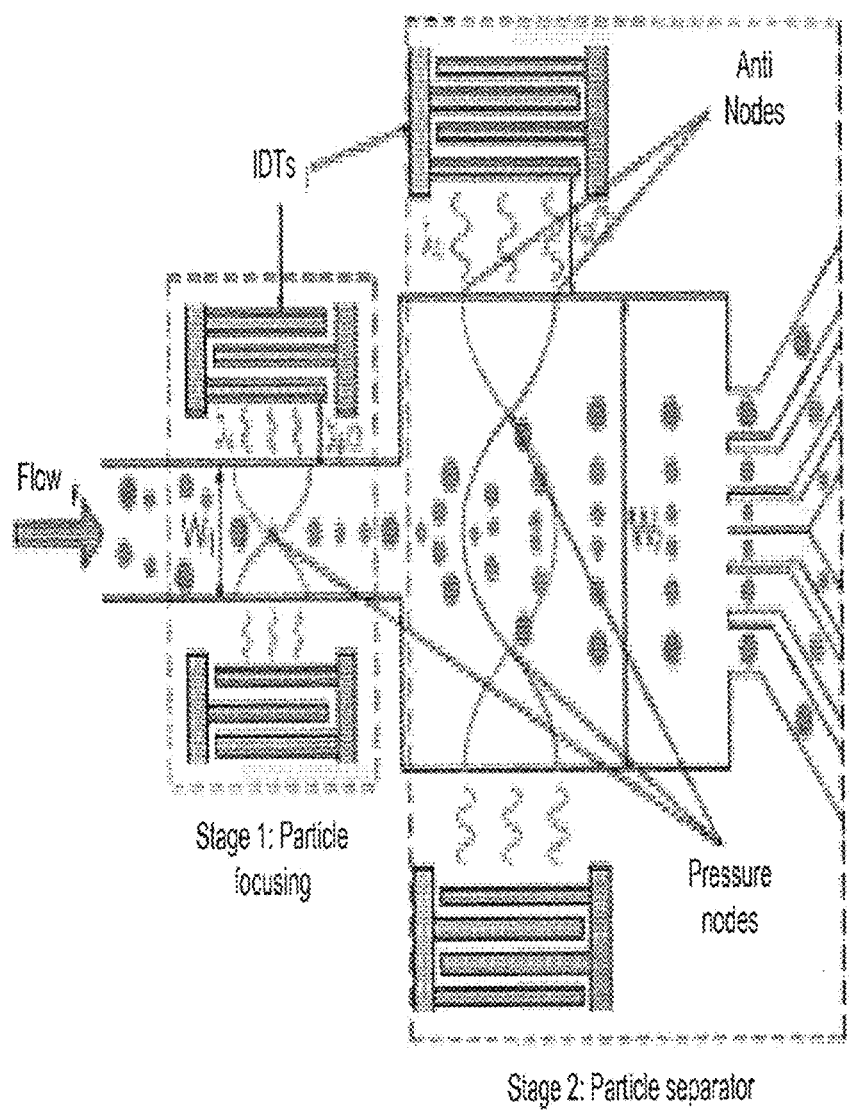
FIG. 4.6

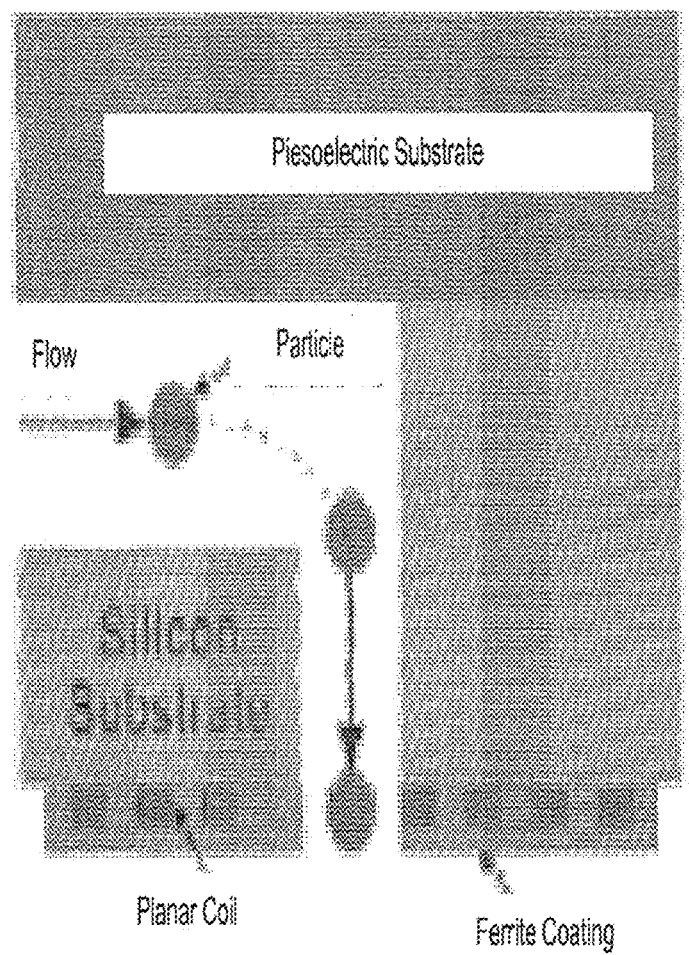
FIG. 4.7

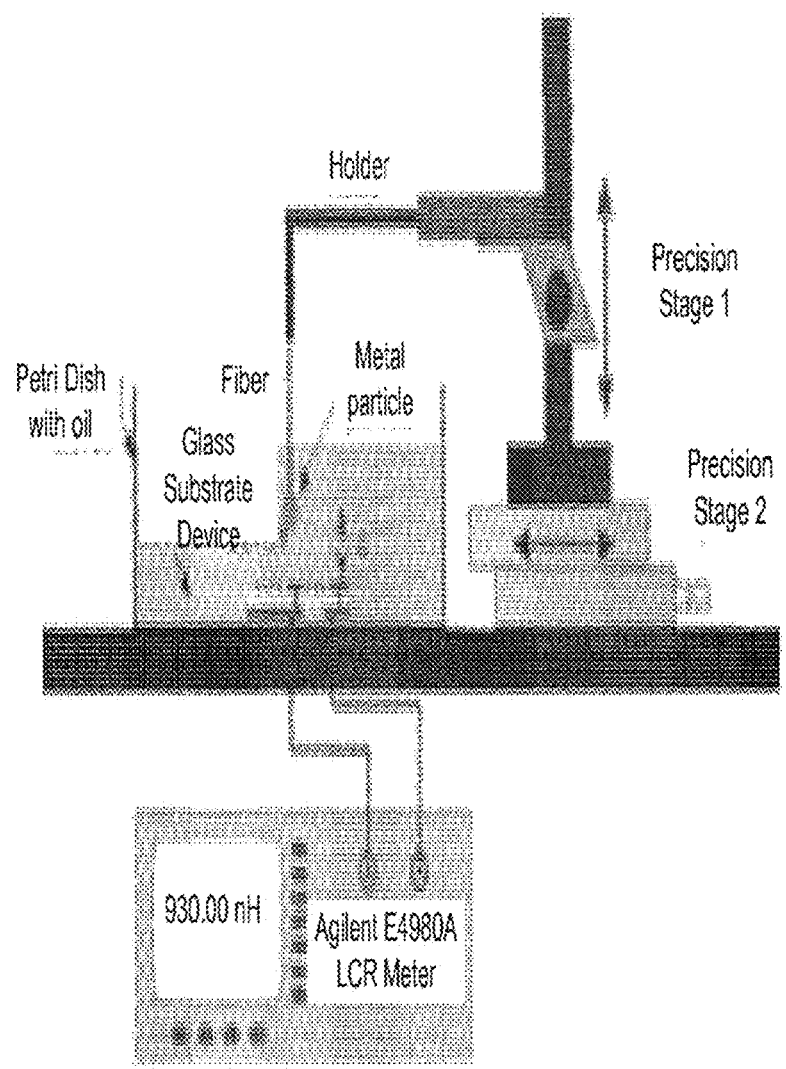
FIG. 4.8

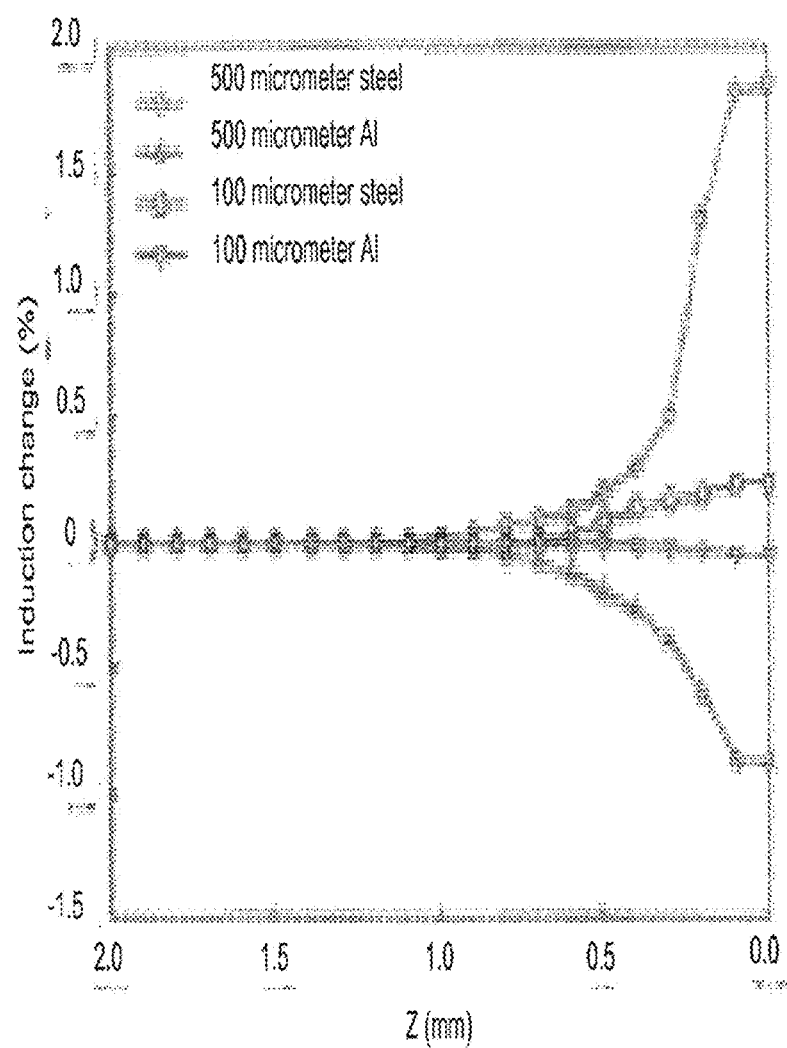
FIG. 4.9

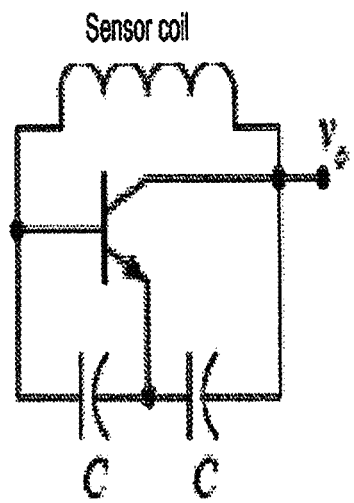
FIG. 4.10
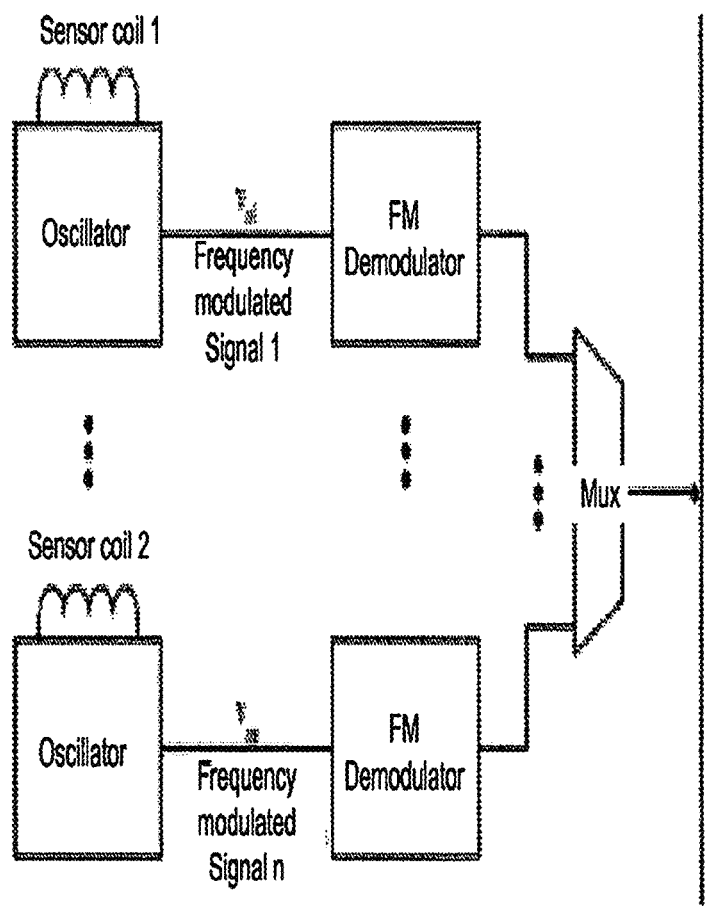
FIG. 4.11

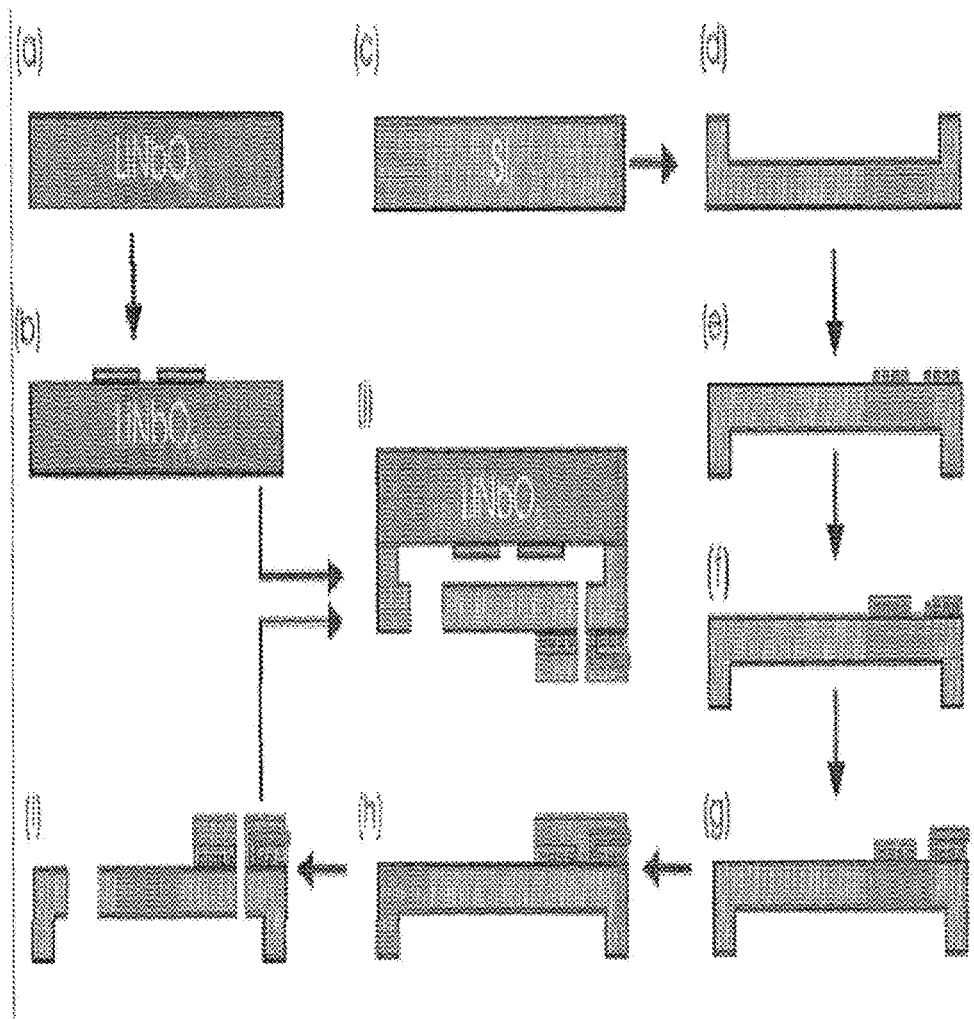
FIG. 4.12

TWO-STAGE MICROFLUIDIC DEVICE FOR ACOUSTIC PARTICLE MANIPULATION AND METHODS OF SEPARATION

CROSS-REFERENCE TO RELATED APPLICATION

This application is a national phase filing of International Application No. PCT/US2012/031526 with an International Filing Date of Mar. 30, 2012, which claims priority from U.S. Provisional Application No. 61/470,124, filed on Mar. 31, 2011, the contents of which are incorporated herein by reference.

FEDERAL SPONSORSHIP

This invention was made with Government support under Contract/Grant No. 0968736, 1135419 and 1056475, awarded by the National Science Foundation. The Government has certain rights in this invention.

BACKGROUND

Cell separation and sorting techniques can be divided into two main categories: (1) methods that require tagging the cells with a label; (2) label-free methods. Flow cytometer is the gold standard for cell separation methods that rely on tagging the cells with labels. Flow cytometer is an instrument for measuring fluorescence and light scattering of individual microscopic particle/cells. Most commonly used flow cytometer techniques are fluorescent activated cell sorting (FACS) and magnetic activated cell sorting (MACS). FACS method utilizes complementary fluorophore-conjugated antibodies to label cells of interests. Although FACS offers high-throughput sorting, there are several technical drawbacks including equipment expense, clogging, contamination, deflection, and cell viability after ejection. Magnetic activated cell sorter (MACS) employs antibody-conjugated, magnetic beads to bind specific proteins on cells of interest. This method is capable of collecting many cells with a relatively low cost. There are, however, several disadvantages to the method including low sensitivity, sensitive process of labeling cells with the magnetic beads and long time frames are requirement for efficient separation. More importantly, both of these cytometer methods require additional "tags" or "labels" to identify cells. However, the biochemical markers may not be available for a specific population. Also, the use of labels may hinder differentiation and they may expand in vitro or in vivo and they add difficulty and cost to the procedure.

Therefore, various label-free cell separation methods have been investigated that address the limitations of flow cytometers. Pinched flow fractionation is a hydrodynamic chromatographic technique capable of separation only by size. As the separation efficiency is based solely on the laminar flow profile in the pinched and broadened segment, cells of varying sizes can be separated effectively by tuning the ratio of the sample to sheath buffer flow rates. However, due to dimension limitation of the pinched segment, separation of small (few microns) particles/cells is very challenging. Also, feasible separation efficiency can only be obtained with very limited flow rates, conflicting with high-throughput system efforts. Hydrodynamic filtration method is another effective way of cell separation, with the separation being determined purely by channel geometry effective. Although this method offers simple operation, the separation efficiency is too low to be a viable separation method. Deterministic lateral displacement technique sort cells exclusively by size using only the geometry of microchannel. Thus, this method does not require external force or field. However, there is a high risk of clogging due to the presence of a large number of high density post structures. Gravitational and sedimentation methods depend on the density, rather than the density of the medium. Separation is simple and does not impose any damaging mechanical stresses on the cells being separated. However, it is limited to the separation of cell populations with relatively large size difference, limiting its use. Optical lattice technique employs three-dimensional arrays of light traps, optical lattices, using holographic optical tweezers. This method has the advantages in term of sensitivity and selectivity. However, the need for laser source prevents the easy portability of the system and continuous system for processing large samples has not been demonstrated due to low separation efficiency. Throughput of this technique also is very limited when compared to flow cytometers. Dielectrophoresis method allows for distinguishing between live and dead cells as well as different types of bacteria by physical properties in addition to size. However, the throughputs of dielectrophoresis are still low when compared to other alternative. Moreover, the cells are often trapped improperly with positive dielectrophoresis and high electric fields could lead to Joule heating and bubble generation as well as heat-related cell death. As a result, none of these methods provides a generic solution to cell separation needs.

SUMMARY

Embodiments of the present disclosure provide for two-stage microfluidic devices using surface acoustic waves, methods of use thereof, methods of making, methods of focusing and separating particles, and the like.

An exemplary embodiment of the present disclosure provides for a two-stage microfluidic device having: a particle focusing stage including: at least a first pair of surface acoustic wave generators, wherein the first pair of surface acoustic wave generators are positioned opposite one another, and a first channel disposed between the first pair of surface acoustic wave generators; a particle separating stage including: a second pair of surface acoustic wave generators, wherein the pair of surface acoustic wave generators are positioned opposite one another, and a second channel disposed between the second pair of surface acoustic wave generators; wherein the first channel and the second channel are in fluidic communication with one another.

An exemplary embodiment of the present disclosure provides for a method of separating particles having: a particle focusing stage including: flowing a plurality of particles into a first channel, wherein the flow is a non-sheath flow, focusing the particles to a first area of the first channel using an interference of a first pair of surface acoustic waves, flowing the plurality of particles along the first area into a second channel, wherein the second channel is in fluidic communication with the first channel, and separating the plurality of particles along a length of the second channel using an interference of a second pair of surface acoustic waves.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 illustrates a schematic of a top view of a two-stage microfluidic device of the present disclosure.

FIG. 2.1 illustrates a schematic view of an embodiment of a two-stage cell separator using surface acoustic waves. The first stage aligns the cells on the center line, while the second stage separates them according to size, density or compressibility. It should be noted that size based separation is illustrated in this figure, but other types of separation are contemplated.

FIG. 2.2A illustrates a schematic of a developed finite element model, while FIG. 2.2B illustrates a preliminary simulation results obtained in the PI's group.

FIG. 2.3 illustrates the lateral displacement of different size particles as a function of time on quartz and lithium niobate substrates. The lithium niobate is more advantageous and is chosen for our device fabrication.

FIG. 2.4 illustrates a schematic of a fabrication process flow.

FIG. 2.5A illustrates a fabricated SAW device patterned on lithium niobate wafer. FIG. 2.5B illustrates the fabricated SU-8 microchannel mold. FIG. 2.5C illustrates the completed two-stage cell separator using surface acoustic waves.

FIG. 2.6 illustrates a schematic diagram of the measurement setup.

FIG. 2.7 illustrates proof of concept experiments conducted with the device illustrated in FIG. 2.5C. The top row illustrates fluorescent images of 10 μm particles (green, lighter color), while the bottom row is for 3 μm particles (red, faint darker color). These images are obtained with a solution containing both particle sizes, but due to the fluorescent filter requirements, the images are presented separately.

FIG. 3.1 illustrates the distribution of acoustic radiation forces within the 2nd stage channel.

FIG. 3.2 illustrates the theoretical analysis of forces acting on particles as a function of particle size.

FIG. 3.3 illustrates the time required for the particle migration toward the pressure node as a function of particle size.

FIG. 3.4 illustrates the experimental setup for the sheathless acoustic particle separation.

FIG. 3.5: (*a*) The chosen location (I-III) in the test section for recording the fluorescent images of the each particle stream; (*b*) Fluorescent images of 10 μm (green) and 3 μm (red) particles distribution. Constant operating frequency of 13.2 MHz, input power of 1 W, flow rate of 0.5 μL/min, and particle concentration of 1% by volume were applied; (*c*) Fluorescent images of 5 μm (green) and 3 μm (red) particles distribution. Constant operating frequency of 13.2 MHz, input power of 1.45 W, flow rate of 0.2 μL/min, and particle concentration of 1% by volume were applied.

FIG. 3.6 illustrates the distribution of each of the two particle sizes (3 and 10 μm) over the two outlets. The acoustic separation efficiency depends on the applied power, flow rate, wavelength of the SAW, channel geometry and particle concentration. Among these parameters, we investigated the effects of the input power, the flow rate, and particle concentration on the separation efficiency as illustrated in FIGS. 3.7, 3.8, and 3.9 respectively. The separation efficiency was defined as A/(A+B) for the 3 μm particles and B/(A+B) for the 10 μm particles, where A is the number of the target particle collected from the center outlet and B is the number of the target particle collected from the side outlets.

FIG. 3.7 illustrates the separation efficiency as a function of input power for 3 and 10 μm particles (driving frequency: 13.2 MHz, flow rate: 0.5 μL/min, particle concentration: 1% by volume).

FIG. 3.8 illustrates the separation efficiency as a function of flow rate for 3 and 10 μm particles (driving frequency: 13.2 MHz, input power: 1 W, particle concentration: 1% by volume).

FIG. 3.9 illustrates the separation efficiency as a function of particle concentration for 3 and 10 μm particles (driving frequency: 13.2 MHz, input power: 1 W, flow rate: 0.5 μL/min).

FIG. 4.1 is a schematic of the proposed microfluidic debris sensor.

FIG. 4.2: (*a*) Schematic of a microfluidic capacitive Coulter counter, and (*b*) capacitive pulses caused by aluminum metal particles in lubrication oil.

FIG. 4.3 shows the schematics of the device that includes a mini-channel wounded by a solenoid at part (*a*), and showing an induced magnetic field at part (*b*), and showing an enhanced magnetic flux at part (*c*), and showing a generated eddy current at part (*d*).

FIG. 4.4 shows the results of mesoscale aluminum and steel particles passing through a microchannel vertically by the force of gravity wherein the V1 (voltage across the solenoid) was recorded for an excitation frequency of 100 kHz.

FIG. 4.5 is a schematic diagram of the working mechanism for the SSAW focusing method.

FIG. 4.6 illustrates the concept of the proposed standing surface acoustic wave (SSAW) particle separator.

FIG. 4.7: Illustration of a single inductive Coulter counting detector.

FIG. 4.8 shows the measurement setup and FIG. 4.9 shows the measured relative inductance change (representing half inductive pulse that would be seen in our proposed device) caused as four different metal particles travel along the z direction; measurements are taken at 2 MHz using an LCR meter.

FIG. 4.10 illustrates instrumentation circuits for which a change in inductance modulates the frequency of an oscillating output voltage.

FIG. 4.11 illustrates a simple multiplexing concept in which the set of outputs from the inductive detectors is combined into a single signal.

FIG. 4.12 shows the basic sequence used to fabricate the devices.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range.

Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of flow dynamics, mechanical engineering, material science, chemistry, and the like, which are within the skill of the art.

The following examples are put forth so as to provide those of ordinary skill in the art with a complete disclosure and description of how to perform the methods and use the structures disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

DISCUSSION

Embodiments of the present disclosure provide for two-stage microfluidic devices, methods of use thereof, methods of making, methods of focusing and separating particles, and the like.

Particle separation is of great interest to many biological and biomedical applications. Current state-of-the-art acoustic based separation technique requires sheath flows for complete separation. Many acoustic-based techniques have been used to spate particles and cells. These standard techniques need one or more sheath flow for successful separation work. However, there are significant disadvantages to employing sheath flow in a microfluidic system, such as dilution of the sample by the sheath fluid, the need for accurate flow control between sample and sheath flow, a complicated multilayered design to introduce sheath flows, and separation efficiency depending on the sheath liquid composition.

In an embodiment, particles are first lined up at the center of the channel without introducing any external sheath flow. After aligning at the center of the channel, the particles are then entered to the actual particle separation stage where the larger particles are exposed to more lateral displacement in the channel towards the pressure node due to the acoustic forces differences. Consequently, different-size particles are separated into multiple collection outlets. The sheathless flow focusing and separation are integrated within a single microfluidic device and accomplished simultaneously. Embodiments of the present disclosure have potential to impact broadly various areas including microfluidic components for lab-on-a-chip system and integrated biological and biomedical applications.

An exemplary embodiment of the present disclosure can use a non-sheath flow for successful separation and incorporate two separate stages with different functions within a single microfluidic channel. In an embodiment, a function of the first stage is to align particles on the center of the microfludic channel without introducing any sheath flow. In an embodiment, the second stage is responsible from the actual separation process. The sheathless flow focusing and separation are integrated within a single microfluidic device and accomplished simultaneously. In proof-of-concept experiments, the separation of two different size particle streams (3 μm and 10 μm) without introducing any external sheath flow was successfully demonstrated.

In general, embodiments of the present disclosure use a two-stage microfluidic device to focus particles (particle focusing stage) and then separate particles (particles separation stage). First, the device uses the interference of a first set of surface acoustic waves to focus the particles in a first channel. The first set of surface acoustic waves can be produced using a pair of surface acoustic wave generators on either side of the first channel. Embodiments of the present disclosure use a non-sheath flow to introduce the particles to the first channel, which is unlike other technologies that use sheath flow. Using a sheath flow is disadvantageous because the analyte of interest is diluted by the sheath fluid, dependence upon the accurate control of the flow rate between the sample and the sheath fluid, and the sheath flow effects the separation, solubility, and/or molecular conformation, which varies among sheath fluids.

Once the particles are focused in the first channel, the particles flow into a second channel. In the second channel a second set of surface acoustic waves are used to separate the particles as the particles flow down the length of the second channel. The second set of surface acoustic waves can be produced using a pair of surface acoustic wave generators on either side of the second channel. Subsequently, the particles of different sizes (e.g., volumes, density, and/or compressibility) can be separated from one another and flow down specific particle channels.

Embodiments of the present disclosure can be used to separate particles such as cells, microparticles, nanoparticles, and aqueous particles and combinations thereof. The types of cells can include plasma, erythrocyte, leukocytes, platelets, circulating tumor cells, and neural stem cells. The microparticles can include polymers particles, metals particles, and pollens. The nanoparticles can include bacteria, yeasts, and polystyrene nanospheres. The aqueous particles in water can include precipitation products, soil colloids, viruses, and protozoa. The diameter of the particles can be about 1 nanometer to 1 micrometer, about 1 µm to 1 mm, or about 3 µm to 10 µm.

Having described embodiments of the present disclosure generally, the following describes specific features of the two-stage microfluidic device. FIG. 1.1 illustrates a schematic of a top view of a two-stage microfluidic device of the present disclosure. The two-stage microfluidic device includes a particle focusing stage (Stage 1) and a particle separating stage (Stage 2). In an embodiment, the particle focusing stage includes a pair of surface acoustic wave generators that each can produce a surface acoustic wave. In an embodiment, the pair of surface acoustic wave generators is positioned opposite one another on either side of the first channel and the generators face one another. In another embodiment, two or more pairs of the surface acoustic wave generators can be used to focus the particles as the particles flow down the length of the first channel.

In an embodiment, the particle separating stage includes a pair of surface acoustic wave generators that each can produce a surface acoustic wave having the same characteristic. In an embodiment, the pair of surface acoustic wave generators is positioned opposite one another on either side of the second channel and the generators face one another. In an embodiment, the first channel and the second channel are in fluidic communication with one another through an interface. In another embodiment, two or more pairs of surface acoustic wave generators can be used to separate the particles as the particles flow down the length of the second channel.

In each of the particle focusing stage and the particle separating stage, each surface acoustic wave generator in each pair produce a set surface acoustic waves. In an embodiment, each set of paired waves has the same wave characteristics (e.g., frequency, power, and wavelength). The paired surface acoustic waves interfere with one another to form a periodic distribution of one or more pressure nodes and anti-nodes on the first channel or the second channel. The interference of the two surface acoustic waves generates a periodic distribution of pressure nodes and an anti-node on the substrate. When each surface acoustic wave reaches the fluid including the particles, leakage waves in longitudinal mode are generated inside the fluid, resulting in the pressure fluctuation. The acoustic radiation forces caused by the pressure fluctuations move the particles toward the pressure nodes or anti-nodes depending on an acoustic contrast factor. Due to the laminar flow behavior of the microfluidics flow, the particles stay in the defined path as the particles flow down the channel even after the acoustic field is removed. The interference pattern of each pair interacts with the particles at each stage, which can be used to focus (stage 1) or separate (stage 2) the particles depending upon the pressure fluctuation pattern and the size of the particles.

In particular, FIG. 1.1 illustrates a single node formed in the first channel from the interference of the first pair of surface acoustic waves, so that all of the particles are focused into a first area along a path that is in-line with the node, which is parallel or substantially parallel the length of the first chamber from the node. The particles flow along the path through the interface and into the second channel. The first area can include a width of about 1 to 10% of the width of the first channel from the node until the interface of the first channel and the second channel. In an embodiment, the characteristics of the surface acoustic waves and/or width of the first channel can be selected so that more than one node can be used to focus the particles into one or more areas along the length of the first channel.

In the second channel, the interference of the two sets of surface acoustic waves produced by the pair of surface acoustic wave generators in the particle separation stage produces two pressure nodes. Particles having different sizes interact with the two pressure nodes, which causes the particles to separate into different paths based on the size of the particles and the acoustic contrast factor. Once separated, the separated particles can be separated into different particle chambers or channels.

In an embodiment, the first channel can be made of a material such as polydimethylsiloxane (PDMS), polyurethanes, polyimides, polymethyl methacrylate (PMMA), silicone, Pyrex™, and combinations thereof. In an embodiment, the first channel can be made of a material such as polydimethylsiloxane (PDMS), polyurethanes, polyimides, and combinations thereof. The thickness of the material used to from the first channel can be about tens of micrometers to tens of millimeters.

In an embodiment, the first channel can have a width of about 10 µm to 2 mm or about 140 µm to 160 µm. In an embodiment, the first channel can have a length of about 1 mm to 20 mm or about 4 mm to 8 mm. In an embodiment, the first channel can have a height of about 10 µm to 200 µm or about 90 µm to 110 µm.

In an embodiment, the interface between the first channel and the second channel can have a width about 10 µm to 2 mm or about 140 µm to 160 µm.

In an embodiment, the second channel can be made of a material such as (PDMS), polyurethanes, polyimides, polymethyl methacrylate (PMMA), silicone, Pyrex™, and combinations thereof. In an embodiment, the second channel can be made of a material such as polydimethylsiloxane (PDMS), polyurethanes, polyimides, and combinations thereof. In an embodiment, the thickness of the material used to from the second channel can be about tens of micrometers to tens of millimeters. In an embodiment, the second channel can have a width of about 20 µm to 4 mm or about 280 µm to 320 µm. In an embodiment, the second channel can have a length of about 0.5 mm to 3 mm or about 0.8 mm to 1.2 mm. In an embodiment, the second channel can have a height of 10 µm to 200 µm or about 90 µm to 110 µm.

In an embodiment, the surface acoustic wave generators (e.g., the first pair and/or second of surface acoustic wave generators) can include interdigitized transducers disposed on piezoelectric substrates and bulk piezoelectric transducers placed on ultrasonic wedges.

In an embodiment, the surface acoustic wave generators can produce acoustic surface waves by varying one or more of the wavelength, frequency, and power. In an embodiment, the wavelength of the surface acoustic wave can be about 20 µm to 4 mm or about 280 µm to 320 µm. In an embodiment, the frequency of the surface acoustic wave can be about 1

MHz to 200 MHz or about 12 MHz to 14 MHz. In an embodiment, the power of the surface acoustic wave can be about 0.2 W to 5 W or about 0.5 W to 1 W.

Referring to FIG. 1.1, the first channel has a width that is half of surface acoustic wave so that only one pressure node occurs at the center of the first channel, while the second channel width is chosen to be the same as the surface acoustic wave wavelength so that the second channel has two pressure nodes. Thus, the width and/or the wavelength of the surface acoustic wave can be designed and/or modified to alter the number of pressure nodes, thereby allowing the two-stage microfluidic device to be designed and operated in the desired mode.

The first pair of surface acoustic wave generators in the particle focusing stage can be positioned about 1 mm to 1.5 mm from the interface of the first channel and the second channel.

The second pair of surface acoustic wave generators in the particle separating stage can be positioned about 0.5 mm to 1 mm from the interface of the second channel and the particle channels.

As mentioned above, the particles can be affected by the interference of surface acoustic waves in each of the first and second stages. In an embodiment, the surface acoustic waves in each of the first stage and the second stage can be independently generated. The interference pattern and the resulting pressure fluctuations cause the particles to move toward the pressure nodes or anti-nodes depending on the acoustic contrast factor. The pressure fluctuations affect the particles based on the size volume, density, compressibility and acoustic contrast factor. In general, since the acoustic force is proportional to the volume of the particles, the larger particles reach the nodes faster than the smaller particles, thereby separating the particles based on size. The strength of the acoustic radiation force depends on the relative density of particle and fluid as well as the relative compressibility of the particle and the fluid as well. The collected particles can be thus separated based on the density and compressibility.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLE 1

Introduction:

An objective of the interdisciplinary effort proposed herein is to explore a novel label-free cell separation platform based on surface acoustic waves that address most limitations of the current state of the art techniques. The separation and sorting of cells are critical for many biological and biomedical applications including cell biology, diagnostics, and therapeutics. For example, the efficient separation of human T-lymphocytes (CD4+) from whole blood is necessary for the diagnosis and treatment of HIV disease [1]. Also, the diagnostic test for malaria takes advantage of separating parasite infected red blood cells from uninfected cells [2]. Currently, there are several methods to separate cells for further analysis in clinical laboratory. One of the gold standards for conventional cell sorter is flow cytometer. Most commonly used flow cytometer techniques are fluorescent activated cell sorting (FACS) and magnetic activated cell sorting (MACS). Although both FACS and MACS offer high-throughput sorting, these expensive methods are limited by the fact that the cells need to be tagged and aligned with a laser/fluorescent source for FACS and labeled with magnetic beads for MACS. However, the biochemical markers may not be available for a specific population, they may hinder differentiation, they may expand in vitro or in vivo and they introduce complexity to the system [3]. Therefore, to address this limitation, label-free cell separation methods—pinched flow fractionation [4, 5], hydrodynamic filtration [6, 7], deterministic lateral displacement [8, 9], sedimentation [10], optical lattice [11, 12], and dielectrophoresis [13, 14]—have been investigated by many researchers. However, each of these methods has significant limitations to make them a universal solution to label-free cell separation as discussed in the background section.

On the other hand, the label-free acoustic based separation methods offer low manufacturing cost, non-invasive operation, ability to sort a vast number of cells, and fast response [15-18]. In addition to separation by size, acoustic based methods enable separation by density, compressibility, acoustic contrast factor as well [15]. Also, it has been shown that the ultrasound does not damage cells or biological samples [19]. Traditionally, bulk acoustic waves (BAW) generated by the substrate-bonded bulk transducers are used for excitation [20, 21]. However, BAW devices require excellent acoustic reflection properties of microfluidic channel material. Unfortunately, many popular channel materials (such as polydimethylsiloxane—PDMS) have very poor reflection coefficients [22]. Additionally, it is difficult to integrate a bulk transducer to a microfluidic chip. More recently, standing surface acoustic wave (SSAW) devices have been investigated addressing these limitations of BAW devices [22, 23]. The SSAWS are generated by interdigitated microelectrodes on piezoelectric substrate and they work on any microchannel materials and can easily be integrated on a complex lab-on-a-chip device. Current SSAW devices require two sheath flows for successful separation. However, introducing sheath flow to a microfluidic channel have several fundamental disadvantages such as dilution of the analyte by the sheath liquid, need for accurate flow control between the sample and sheath flow and separation efficiency strongly depending on the sheath liquid composition [24].

In this Example, a novel SSAW based cell separation technique is presented that addresses many, and potentially many, of the limitations of current state of the art label-free cell separation techniques. By taking advantage of microfabrication flexibilities, we incorporate two separate stages with different functions within a single microfluidic device. The sole function of the first stage is to align cells on the center of the microfludic channel without introducing any sheath flow. The second stage is responsible from the actual separation process (FIG. 2.1). The microchannel width of the first stage is designed to be half of SAW wavelength so that only one pressure node occurs at the center of the channel, while the channel width of the second stage is chosen to be SAW wavelength so that the channel has two pressure nodes. For the operation of the device, two interdigitated transducer (IDT) pairs are patterned on a piezoelectric substrate to generate the SAWs and a microfluidic channel is aligned at half way between the IDT pairs. For size based separation, in the second stage of the design, the larger cells is exposed to more lateral displacement in the channel towards the pressure node due to the difference in acoustic forces acting on them. Hence, different size cells are accumulated into multiple collection outlets as illustrated schematically in FIG. 2.1. In an embodiment, this approach should enable us to separate cells based on acoustic force difference (not only size difference but also density, compressibility and acoustic contrast factor).

Embodiments of the present disclosure can be used for detection and analysis of circulating tumor cells (CTCs), separation of neural stem cells, and separation of leukocytes, red blood cells, and platelets from whole blood, for example.

Continuous separation and sorting of biological cells can be performed with acoustic forces generated by ultrasonic waves [15-18]. In addition to separation by size, acoustic based methods enable separation by density, compressibility, acoustic contrast factor as well [15]. For example, an interesting application of acoustic separation method is the purification of blood from lipid droplets during open heart surgery. The acoustic force on red blood cells suspended in plasma pushes the cells towards pressure nodes, whereas lipid droplets are pushed towards pressure antinodes due to acoustic contrast differences [29]. The acoustic based method is an ideal cell manipulation method for lab-on-a-chip devices because this method features low manufacturing cost, non-invasive nature, ability to sort vast number of cells, and fast response time. The ultrasonic methods do not damage cells as well [19]. Recent studies demonstrated separation and manipulation of cells in microfluidic channels by using bulk acoustic wave (BAW) bonded to the substrate [20, 21]. However, the generation of bulk acoustic wave requires high acoustic reflection coefficient of the microfluidic channel material. This requirement makes the bulk acoustic wave devices not applicable to many microfluidic devices made of materials with poor acoustic reflection, such as polydimethylsiloxane (PDMS) [22]. Additionally, it is difficult to integrate a bulk transducer to a microfluidic chip. Recently, standing surface acoustic waves (SSAW), generated by interdigitated microelectrodes on piezoelectric substrate, has been demonstrated to manipulate E-coli and blood cells in microchannels [22, 23]. This technique works for any microchannel materials and can be easily incorporated into a multi-stage device because of its simplicity. However, two sheath flows were used to align a particle stream and to prevent particles from trapping and aggregating along the sidewall of the microchannel. Introducing sheath flow to the microfluidic channel has several disadvantages: (1) dilution of the analyte by the sheath liquid; (2) need for accurate flow control between the sample and sheath flow; (3) separation efficiency strongly depends on the sheath liquid composition [24]. Therefore, there is a need to investigate sheathless flow methods for separating various cells in suspension by using surface acoustic waves for significant biomedical applications.

In an embodiment of the present disclosure, there are two-stages that serve different functions within a single microfluidic channel as schematically illustrated in FIG. 2.1. The first stage is designed to align the cells at the center of the microfluidic channel by surface acoustic waves without adding any external sheath flow. Note that our experiments with preliminary devices illustrate that the particles even attached to the channel walls are aligned at the center of the channel in the first stage. The second stage is responsible from separating the cells according to size, density, compressibility and acoustic contrast factor. The microchannel width of the first stage is designed to be half of SAW wavelength so that single pressure node coincides with the center of the channel, while the channel width of the second stage is chosen to be SAW wavelength so that the channel has two pressure nodes (FIG. 2.1). For the operation of the device, two interdigitated transducer (IDT) pairs are patterned on a piezoelectric substrate and a microfluidic channel is aligned at half way between the IDT pairs. When the two IDTs are applied with a RF signal, two series of surface acoustic waves propagate in opposite directions toward the cell solution inside the microchannel. The interference of the two surface acoustic waves generates the periodic distribution of pressure nodes and anti-node on the substrate. When surface acoustic wave reach the medium, leakage waves in longitudinal mode are generated inside the medium, resulting in the pressure fluctuation. The acoustic radiation forces caused by the pressure fluctuations move the cells toward the pressure nodes or anti-nodes depending on the acoustic contrast factor. Due to the laminar flow behavior of the microfluidics flow, the cells will stay in the defined position even after the acoustic force field is removed. For size based separation, since the acoustic force is proportional to the volume of the cells, larger cells are subjected to larger acoustic force. After passing the first stage, due to this difference in magnitude of the acoustic forces acting on cells, the larger cells reaches the pressure node in less time than does the smaller cells. As a result, the cells are repositioned with different lateral displacement along the cross-section of the channel, which is split into multiple collection outlets (FIG. 2.1). It is important to note that our approach is capable of cell separation based on not only size, but also by density, compressibility, or acoustic contrast factor.

Theoretical Analysis and Finite Element Simulation Models:

The studies that investigated cell separation using surface acoustic waves were all experimental studies [15-18]. Hence, there is very little known about how the waves interact with cells, or even optimal design parameters of the interdigitated transducer (IDT) for an efficient separation system. We, therefore, will develop finite element and theoretical models to study the wave propagation characteristics of surface acoustic waves and IDT design parameters for optimum design. As the motion of the fluid is strongly coupled to the microfluidic channel, we will develop transient coupled field finite element models with advanced fluid-structure interface (FSI), in ANSYS v12.0. Modeling only the microfludic channel part (without the substrate part that houses the IDTs) will be sufficient as that's where the separation is occurring. The finite element model with advanced fluid-structure interface (FSI) model can include of five major components: the transducer (to generate the surface acoustic waves), the microfluidic channel, the fluid, the fluid-structure interface, and the absorbing boundary as illustrated schematically in FIG. 2.2a. The fluid in the simulation is assumed to be linear and lossless and modeled by employing FLUID30 elements. In the FSI model, a system of four coupled wave equations for the electric potential and the three component of displacement are solved for the solid domain. These coupled wave equations can be discretized and solved for generating displacement profiles and voltages at each element/node which are applied to the fluid domain at each time step. Fluid domain would be modeled using the Navier-Stokes equation. Since transient analysis will be carried out to obtain response, an absorbing boundary condition is required to prevent waves from reflecting from the model edges and generating an unrealistic wave field in the fluid region. This absorbing boundary layer is modeled by FLUID130®. However, there is no absorbing boundary condition for the solid substrate in ANSYS®, hence highly attenuating material with small stiffness multiplier for Rayleigh damping equation is used to attenuate the surface acoustic waves that is propagating in the substrate. This prevents the reflection of surface acoustic waves from solid substrate edges and generating unrealistic standing waves. Microfluidic channel and the solid absorbing boundary layers are modeled by using SOLID45® elements. FIG. 2.2B illustrates preliminary transient wave propagation results from our model housing all five components. The propagating surface acoustic wave is clearly observed from the model, note that there are spurious bulk acoustic waves propagating perpendicular to the transducer but they will be attenuated by the absorbing boundary. This advanced simulation model will enable us to investigate the effect of substrate type, the design parameters of IDT such as the acoustic aperture, the number of finger pairs, the width and gap between fingers, the distance between IDTs on the separation efficiency.

Theoretical Cell Displacement:

Cell displacement and trajectory analysis by considering various forces on cells enables design optimization of the second stage. This analysis can also be used to optimize flow rates for separation and acoustic energy density to maximize the device efficiency, minimizing power requirements. The current simplified model takes gravity, buoyancy, viscous and acoustic radiation forces into account [22]. Based on the Stokes' law, the viscous force can be expressed as $$F_v = 6\pi \mu r v \quad (1)$$

where $\mu$, $r$, $v$ represent medium viscosity, the cell radius, and relative velocity of cells with respect to medium, respectively. The acoustic radiation force can be expressed as $$F_{ac} = -\left(\frac{\pi p_o^2 V_p \beta_m}{2\lambda}\right) \phi(\beta, \rho) \sin\left(\frac{4\pi x}{\lambda}\right) \quad (2)$$

$$\phi = \frac{5\rho_p - 2\rho_m}{2\rho_p + \rho_m} - \frac{\beta_p}{\beta_m} \quad (3)$$

where $p_o$, $\lambda$, $V_p$, $x$ are the acoustic pressure amplitude, ultrasonic wavelength, cell volume, and distance from a pressure node, respectively. It is important to note that when cells maintain constant velocity in the surface acoustic wave field, the acoustic and viscous balance each other. Hence, the velocity can be obtained as $$v = -\left(\frac{p_o^2 V_p \beta_m}{12\lambda \mu r}\right) \phi(\beta, \rho) \sin\left(\frac{4\pi x}{\lambda}\right) \quad (4)$$

Rewriting $$v = -\frac{dx}{dt}$$

and separating variables gives us, $$\mathrm{Cosec}\left(\frac{4\pi x}{\lambda}\right) dx = \left(\frac{p_o^2 V_p \beta_m}{12\lambda \mu r}\right) \phi(\beta, \rho) dt \quad (5)$$

Since the cells will move to the pressure nodes nearby, $dx$ should be in the range of $(0, \lambda/4)$. Therefore, the time needed for cell migration will be $$t = ((3\lambda \uparrow 2 \mu r)/\pi) \quad (6)$$

-continued $$([\ln(\tan(2\pi x/\lambda)) \downarrow (x \downarrow 1)^\uparrow (x \downarrow 2))/[[p \downarrow o]]^\uparrow 2V \downarrow p\beta \downarrow m\phi(\beta, \rho)]$$

where $$x_1 = 0.01\left(\frac{\lambda}{4}\right)$$

and $$x_2 = 0.99\left(\frac{\lambda}{4}\right)$$

We calculated response time for the agglomeration process for 3, 10, and 15 μm polystyrene particles at different substrates (FIG. 2.3). As predicted, the larger particles move to the pressure node quicker than the smaller particles due to the acoustic forces difference. The acoustic pressure amplitude in Equation 4 depends on the applied power and the density and surface acoustic wave velocity of substrate. Since the density and surface acoustic wave velocity of lithium niobate are larger than that of quartz, the particles on the lithium niobate are subjected to larger acoustic force than on quartz, reaching the pressure node quicker. It is important to note that this simplified analysis does not consider many factors such as cell concentration and flow velocity profile.

Device Design:

The finite element models developed (Task 1) and theoretical equations are employed to obtain the physical dimensions and performance metrics of the SAW transducers and the separation system. The IDT finger pitch defines the SAW wavelength. In the preliminary device designs, the SAW wavelength, the IDT finger pitch, and finger width are choosen as 300 μm, 300 μm, and 75 μm, respectively. Acoustic aperture was selected to be 25λ (7.5 mm) as aperture of less than approximately 20λ is inadvisable for 50Ω IDT impedance system [30]. The number of finger pairs in the IDTs affects the bandwidth of the transducer. The narrower bandwidth due to large number of finger pairs results in higher stability and lower oscillator noise. However, when the number of finger pairs exceeds about 100, the losses associated with mass loading and scattering from the electrodes begin to neutralize any additional advantage [31]. So, we selected a typical value, 25 pairs. The channel width of the first stage was 150 μm, a half of SAW wavelength, to contain only one pressure node in the center of the channel. On the other hand, second stage width was 300 μm, the same as SAW wavelength, to have two pressure nodes in the channel. The channel lengths were determined based on the results of preliminary quantitative force analysis (section C.1.1). The lithium niobate (LiNbO$_3$) wafer and 3, 10 μm polystyrene particles were used for the preliminary testing. For 1 mm/s for flow velocity, the channel length of first stage should be larger than 3.5 mm to focus smaller particle (3 μm) and the channel length of second stage should be selected to prevent smaller particle move to the pressure node. However, even if the length of channel is fixed the separation efficiency can be adjusted by tuning the input power and the flow rate. The resonance frequency of the SAW is determined by the ratio of the SAW velocity ($V_{SAW}$) in the substrate and SAW wavelength $$(\lambda); f = \frac{V_{SAW}}{\lambda}.$$

TABLE 1

Preliminary design parameters used for proof of concept experiments

| | |
|---|---|
| Wavelength (λ) | 300 μm |
| IDT finger width | 75 μm (0.25λ) |
| IDT finger pitch | 300 μm (λ) |
| IDT finger pairs | 25 pairs |
| IDT aperture | 7.5 mm (25λ) |
| Distance between IDTs | 9 mm (30λ) |
| Channel width | 150 μm (0.5λ, $1^{st}$ stage) |
| | 300 μm (λ, $2^{nd}$ stage) |
| Channel height | 100 μm |
| Channel length | 8 mm ($1^{st}$ stage) |
| | 1 mm ($2^{nd}$ stage) |
| Input power | 0.5-1 W |
| Frequency | 13.2 MHz |
| Flow rate | 0.5-5 μl/min |

With the SAW velocity 3970 m/s for the chosen SAW direction on the substrate (LiNbO$_3$) the resonance frequency turns out to be 13.2 MHz. Table 1 shows the values of the design and working parameters for the preliminary device. Note that once we obtain more accurate simulation and theoretical models (task 1), we will do design optimization for obtaining the most efficient cell separation platform with minimum power consumption.

Device Fabrication and Integration:

There are three major steps involved in the fabrication of the two-stage cell separator: the fabrication of IDTs on substrate, the fabrication of the PDMS microchannel, and the bonding of the PDMS microchannel and the IDT substrate. FIG. 2.4 illustrates the fabrication process flow. For the fabrication of IDT substrate, a two-side polished Y+128° X-propagation lithium niobate (LiNbO$_3$) wafer are used. A 100 nm thick chrome layer is deposited on the lithium niobate wafer using CRC sputter. The lithium niobate wafer is then coated with 1.6 μm-thick photoresist (S1813, Shipley, Marlborough, Mass.), patterned with a UV light source, and developed in a photoresist developer (MF 319, Shipley, Marlborough, Mass.). The chrome layer is then etched using chrome etchant (CR-7S, Cyantek, Fremont, Calif.). Finally, the photoresist is removed by the PR remover. The fabricated IDTs on the lithium niobate substrate are shown in FIG. 2.5a.

The microfluidic channel is fabricated with PDMS (Poly-DiMethylSiloxane) micromolding technique. The mold is patterned on the silicon wafer by 100 μm-thick negative photoresist (SU-8 2075, MicroChem, Newton, Mass.). The PDMS oligomer and crosslinking prepolymer of PDMS agent from a Sylgard™ 184 kit (Dow Corning, Midland, Mich.) is mixed in a weight ratio of 10:1, poured onto the SU-8 mold, and then cured at room temperature for 24 hours more in order to prevent PDMS shrinking due to a heat. After PDMS replica is peeled off from the mold, the inlets and outlets are generated using the biopsy punch. The fabricated microchannel mold is shown in FIG. 2.5b.

For bonding the PDMS microchannel to the substrate containing IDTs, oxygen plasma (5 minutes at 25 sccm oxygen flow rate, 500 mTorr chamber pressure, and 100 W power) is utilized to activate both surfaces. After ethanol acting as lubricant is dropped on the surface of IDT substrate, the alignment of the PDMS microchannel and IDT substrate are conducted. To remove ethanol, the aligned device is placed in a vacuum chamber, and then PTFE tubings are connected to the fabricated device. FIG. 2.5c illustrates a complete two-stage microfluidic device (with preliminary design parameters shown in Table 1) including the PDMS microchannel and IDT substrate that is used for proof of concept demonstrations.

Experimental Characterization and Model Verification:

The first step is to measure the electrical impedance of individual transducers via a network analyzer (ENA E5061A). This vital data provides the operation frequency and uniformity which are important verification parameters for our design, fabrication and simulations. For proof-of-concept demonstrations, an experiment is conducted with preliminary device on an inverted microscope (Ti-U, Nikon). A mixture solution of polystyrene particles (Thermo Scientific, Waltham, Mass.) with diameters of 3 μm (red) and 10 μm (green) is injected into the microchannel by a syringe pump (KDS200, KD Scientific, Holliston, Mass.). An AC signal is generated by a signal generator (AFG3022B, Tektronix) and then amplified by a RF power amplifier (325LA, ENI). The signal is split two ways to provide identical signals to the IDTs and generate SAWs (FIG. 2.6). The distribution of each particle was captured during the separation process at three different locations marked as (a), (b) and (c) in FIG. 2.7. Each image was taken at the same position with different excitation light. Location (a) was before the particles enter the first stage. One can clearly observe that both particle sizes were scattered in the channel. When particles entered the first stage (location (b)), the acoustic forces acting on particles align them at the center of the channel where pressure nodes existed. Location (c) coincides with the second stage of the device. As can be observed from FIG. 2.7, 10 μm particles move to the pressure nodes while 3 μm particles remained in the center of the channel because the acoustic forces exerted were insufficient to push them into the pressure nodes. As a result, the larger particles were separated to the side channels and the smaller particles were separated to the center channel. This significant experiment showed that our platform is capable of separating different size particles based on surface acoustic waves without introducing any external sheath flow to the microfluidic channel.

This experiment was conducted with the sole purpose of demonstrating that our concept does indeed work as hypothesized with the non-optimized preliminary device (with design parameters illustrated in Table 1). However, this experiment does not give us insight on the capabilities and limitations of our approach, or how optimized our design is. To investigate this, after we conduct our design optimization studies with the proposed advanced simulation and in-depth theoretical analysis, we will conduct similar characterization experiments to obtain separations efficiency among other significant parameters. These experiments will also allow us to verify the optimization studies (task 1) and necessary changes will be implemented to the simulation and theoretical models. During the experiments, cell samples will be collected from the outlets to quantitatively evaluate the separation efficiency. Public domain ImageJ® program will be used to count the number of cells collected from each outlet. We will analyze the ratio of the cells collected from the side channels after applying SAW to the cells prior to SAW exposure as well as the ratio of the cells collected from the central channel after applying SAW to the cells prior to SAW exposure to evaluate the separation efficiency.

Application of the Two-Stage Cell Separator

The two-stage cell separator using SAW can be used in a variety of biomedical applications. Many diagnostic tests depend on fractionated blood components: plasma, red blood cells (erythrocyte), white blood cells (leukocytes), and platelets. Clean, cell-free plasma is necessary for early cancer detection by blood-borne cancer biomarkers [32, 33].

Also, white blood cells or leukocytes are required for several hematological tests as well as DNA sequencing. Moreover, the preparation of platelet concentrates is a time-consuming and costly procedure. So, it is of great interest to find cost-effective methods with high purity and yield. The separation of leukocytes, red blood cells, and platelets from whole blood can be achieved by the present separator based on their sizes. One of major health care problems is the lack of allogeneic blood (donor blood). To reduce this demand, shed blood can be collected and returned to the patient during or after surgery, called autologous blood recovery. The recent autologous blood recovery techniques are based on centrifuges. A large volume of shed blood is collected and centrifuged, and then the supernatant is removed and the collected erythrocytes are subsequently returned to the patient. However, this method cannot remove lipids derived from surgery of adipose tissue efficiently and therefore offers no solution to the lipid emboli problem [29]. Also, the erythrocytes experience high gravitational forces deforming them during the centrifugation process, and centrifugation is known to induce hemolysis [34]. Finally, the process is not continuous and demands a large volume of blood to initiate a cell wash cycle which makes it inappropriate for many applications. The present technique can be used to remove lipids from erythrocytes in whole blood without the above problems. Since the lipids and erythrocyte in blood plasma have the different sign of the acoustic contrast factor, $\phi \approx 0.3$ and $\phi \approx -0.3$ respectively, they can be separated by the based on their compressibility and density.

The detection and analysis of circulating tumor cells (CTCs), is important for fundamental understanding of the process of metastasis, disease staging, predicting prognosis, monitoring patients during therapy, and improving therapy design. Because CTC numbers can be very small, these cells are not easily detected [35]. However, the isolation of CTCs from whole blood can be performed based on cell size because CTCs commonly are larger than blood components. The present technique is widely applicable because no prior information about cell surface markers or DNA abnormalities is required. Only a simple dilution of the whole blood is required before loading of the sample onto our lab-on-a-chip device.

The separation of neural stem cells is of critical importance to understanding the specific and unique functions. These cells play a significant role in the central nervous system (CNS), and potential applications in cell replacement therapy in many neurodegenerative disorders (such as Parkinson's, Alzheimer's, or Multiple sclerosis) and cancer [36, 37]. The separation of neural stem cells from progenitor cells can be accomplished based on the size. The present method can greatly reduce the amount of time required for cell purification and preparation for transplantation compared to the use of FACS for the purification of hematopoietic stem cells which can take 1-17 hours [38]. The separation of neural stem cells based on the size does not require the specific labeling of cells, and therefore offers the possibility of cell purification of mixtures of cells where distinct cell surface markers for the different types of cells in the population are not available, or when cell labeling with antibodies or other cell markers is not desired.

References, each of which is incorporated by reference:

[1] X. H. Cheng, et al., "A microfluidic device for practical label-free CD4+T cell counting of HIV-infected subjects," *Lab on a Chip*, vol. 7, pp. 170-178, 2007.

[2] P. Gascoyne, et al., "Microfluidic approaches to malaria detection," *Acta Tropica*, vol. 89, pp. 357-369, February 2004.

[3] B. Roda, et al., "A Tag-Less Method of Sorting Stem Cells from Clinical Specimens and Separating Mesenchymal from Epithelial Progenitor Cells," *Cytometry Part B-Clinical Cytometry*, vol. 76B, pp. 285-290, July 2009.

[4] J. Takagi, et al., "Continuous particle separation in a microchannel having asymmetrically arranged multiple branches," *Lab on a Chip*, vol. 5, pp. 778-784, 2005.

[5] M. Yamada, et al., "Pinched flow fractionation: Continuous size separation of particles utilizing a laminar flow profile in a pinched microchannel," *Analytical Chemistry*, vol. 76, pp. 5465-5471, Sep. 15, 2004.

[6] M. Yamada, et al., "Microfluidic devices for size-dependent separation of liver cells," *Biomedical Microdevices*, vol. 9, pp. 637-645, October 2007.

[7] M. Yamada and M. Seki, "Hydrodynamic filtration for on-chip particle concentration and classification utilizing microfluidics," *Lab on a Chip*, vol. 5, pp. 1233-1239, 2005.

[8] L. R. Huang, et al., "Continuous particle separation through deterministic lateral displacement," *Science*, vol. 304, pp. 987-990, May 14, 2004.

[9] B. R. Long, et al., "Multidirectional sorting modes in deterministic lateral displacement devices," *Physical Review E*, vol. 78, pp.-, October 2008.

[10] D. Huh, et al., "Gravity-driven microfluidic particle sorting device with hydrodynamic separation amplification," *Analytical Chemistry*, vol. 79, pp. 1369-1376, Feb. 15, 2007.

[11] M. P. MacDonald, et al., "Microfluidic sorting in an optical lattice," *Nature*, vol. 426, pp. 421-424, Nov. 27, 2003.

[12] A. T. Ohta, et al., "Optically controlled cell discrimination and trapping using optoelectronic tweezers," *Ieee Journal of Selected Topics in Quantum Electronics*, vol. 13, pp. 235-243, March-April 2007.

[13] J. M. Caicedo and S. J. Dyke, "Experimental validation of structural health monitoring for flexible bridge structures," *Structural Control & Health Monitoring*, vol. 12, pp. 425-443, July-December 2005.

[14] I. F. Cheng, et al., "A continuous high-throughput bioparticle sorter based on 3D traveling-wave dielectrophoresis," *Lab on a Chip*, vol. 9, pp. 3193-3201, 2009.

[15] S. Kapishnikov, et al., "Continuous particle size separation and size sorting using ultrasound in a microchannel," *Journal of Statistical Mechanics-Theory and Experiment*, pp.-, January 2006.

[16] A. Nilsson, et al., "Acoustic control of suspended particles in micro fluidic chips," *Lab on a Chip*, vol. 4, pp. 131-135, 2004.

[17] J. J. Shi, et al., "Focusing microparticles in a microfluidic channel with standing surface acoustic waves (SSAW)," *Lab on a Chip*, vol. 8, pp. 221-223, 2008.

[18] M. Wiklund, et al., "Ultrasonic standing wave manipulation technology integrated into a dielectrophoretic chip," *Lab on a Chip*, vol. 6, pp. 1537-1544, December 2006.

[19] F. S. Foster, et al., "Advances in ultrasound biomicroscopy," *Ultrasound in Medicine and Biology*, vol. 26, pp. 1-27, January 2000.

[20] H. Jonsson, et al., "Particle separation using ultrasound can radically reduce embolic load to brain after cardiac surgery," *Annals of Thoracic Surgery*, vol. 78, pp. 1572-1578, November 2004.

[21] F. Petersson, et al., "Free flow acoustophoresis: Microfluidic-based mode of particle and cell separation," *Analytical Chemistry*, vol. 79, pp. 5117-5123, Jul. 15, 2007.

[22] J. J. Shi, et al., "Continuous particle separation in a microfluidic channel via standing surface acoustic waves (SSAW)," *Lab on a Chip*, vol. 9, pp. 3354-3359, 2009.
[23] J. J. Shi, et al., "Acoustic tweezers: patterning cells and microparticles using standing surface acoustic waves (SSAW)," *Lab on a Chip*, vol. 9, pp. 2890-2895, 2009.
[24] M. A. Strege and A. L. Lagu, "Capillary Electrophoresis as a Tool for the Analysis of Protein-Folding," *Journal of Chromatography A*, vol. 652, pp. 179-188, Oct. 15, 1993.
[25] M. R. Melamed, "A brief history of flow cytometry and sorting," *Methods in Cell Biology, Vol 63*, vol. 63, pp. 3-17, 2001.
[26] A. Y. Fu, et al., "A microfabricated fluorescence-activated cell sorter," *Nature Biotechnology*, vol. 17, pp. 1109-1111, November 1999.
[27] S. Miltenyi, et al., "High-Gradient Magnetic Cell-Separation with Macs," *Cytometry*, vol. 11, pp. 231-238, 1990.
[28] M. Kersaudy-Kerhoas, et al., "Recent advances in microparticle continuous separation," *let Nanobiotechnology*, vol. 2, pp. 1-13, March 2008.
[29] F. Petersson, et al., "Separation of lipids from blood utilizing ultrasonic standing waves in microfluidic channels," *Analyst*, vol. 129, pp. 938-943, 2004.
[30] G. T. A. Kovacs, *Micromachined Transducers Sourcebook*. New York, N.Y.: McGraw-Hill, 1998.
[31] D. S. Ballantine and R. M. White, *Acoustic Wave Sensors*: Academic Press, 1997.
[32] J. N. Li, et al., "Proteomics and bioinformatics approaches for identification of serum biomarkers to detect breast cancer," *Clinical Chemistry*, vol. 48, pp. 1296-1304, August 2002.
[33] J. Villanueva, et al., "Differential exoprotease activities confer tumor-specific serum peptidome patterns," *Journal of Clinical Investigation*, vol. 116, pp. 271-284, January 2006.
[34] C. T. Klodell, et al., "Does cell-saver blood administration and free hemoglobin load cause renal dysfunction?," *American Surgeon*, vol. 67, pp. 44-47, January 2001.
[35] M. Cristofanilli, et al., "Circulating tumor cells, disease progression, and survival in metastatic breast cancer," *New England Journal of Medicine*, vol. 351, pp. 781-791, Aug. 19, 2004.
[36] E. Hedlund, et al., "Selection of embryonic stem cell-derived enhanced green fluorescent protein-positive dopamine neurons using the tyrosine hydroxylase promoter is confounded by reporter gene expression in immature cell populations," *Stem cells*, vol. 25, pp. 1126-1135, 2007.
[37] J. A. Korecka, et al., "Cell-replacement and gene-therapy strategies for Parkinson's and Alzheimer's disease," *Regenerative Medicine*, vol. 2, pp. 425-446, July 2007.
[38] C. Reading, et al., "Clinical-Scale Purification of Cd34+Thy-1+Lin−Stem Cells from Mobilized Peripheral-Blood by High-Speed Fluorescence-Activated Cell Sorting for Use as an Autograft for Multiple-Myeloma Patients," *Blood*, vol. 84, pp. A399-A399, Nov. 15, 1994.

EXAMPLE 2

Brief Introduction:

Particle separation is of great interest in many biological and biomedical applications. Flow-based methods have been used to sort particles and cells. However, the main challenge with flow based particle separation systems is the need for a sheath flow for successful operation. Existence of the sheath liquid dilutes the analyte, necessitates precise flow control between sample and sheath flow, requires a complicated design to create sheath flow and separation efficiency depends on the sheath liquid composition. In this paper, we present a microfluidic platform for sheathless particle separation using standing surface acoustic waves. In this platform, particles are first lined up at the center of the channel without introducing any external sheath flow. The particles are then entered into the second stage where particles are driven towards the off-center pressure nodes for size based separation. The larger particles are exposed to more lateral displacement in the channel due to the acoustic force differences. Consequently, different-size particles are separated into multiple collection outlets. The prominent feature of the present microfluidic platform is that the device does not require the use of the sheath flow for positioning and aligning of particles. Instead, the sheathless flow focusing and separation are integrated within a single microfluidic device and accomplished simultaneously. In this paper, we demonstrated two different particle size-resolution separations; (1) 3 µm and 10 µm and (2) 3 µm and 5 µm. Also, the effects of the input power, the flow rate, and particle concentration on the separation efficiency were investigated. These technologies have potential to impact broadly various areas including the essential microfluidic components for lab-on-a-chip system and integrated biological and biomedical applications.

Introduction:

The separation of particles or cells is critical for many biological and biomedical applications, including cell biology, diagnostics and therapeutics. For instance, efficient separation and quantification of human T-lymphocytes (CD4+) from whole blood is necessary for the monitoring and treatment of HIV [1]. Also, the diagnostic test for malaria depends on the separation of parasite infected red blood cells from uninfected cells [2]. Particle separation is particularly important for multichannel resistive/inductive pulse microparticle sensors [3-5] whose sensitivity is proportional to the ratio of particle/microchannel size. For these types of sensors, size-dependent particle separation would allow different-sized micro/nano particles to be guided to different sensing channels with corresponding sizes, thus greatly improving the sensitivity and dynamic range at a high throughput. To date various techniques for particle or cell separation have been studied including hydrodynamic filtration [6,7], deterministic lateral displacement [8,9], pinched flow fractionation [10,11], sedimentation [12], inertial [13,14], magnetophoresis [15,16], negative magnetophoresis [17,18], optical [19,20] and dielectrophoresis [21, 22]. Separation of biological particles, e.g., cells, can be performed using acoustic forces. When particles in a medium are subjected to an acoustic wave field, they experience pressure gradients. These pressure gradients can be used to manipulate suspended particles [23-26]. The acoustic-based method is an ideal particle or cell manipulation method for lab-on-a-chip devices, since this label-free method features low manufacturing cost, non-invasive nature, ability to separate a vast number of particles, and fast response time. Recent studies demonstrated the separation and manipulation of particles in microchannels using bulk acoustic waves generated by substrate-bonded bulk transducers [27-29]. However, the generation of bulk acoustic waves requires a high acoustic reflection coefficient of the microfluidic channel material. This requirement makes the bulk acoustic wave approach not applicable to many microfluidic devices that utilize commonly used materials with poor acoustic reflection such as polydimethylsiloxane (PDMS) [30]. Furthermore, since bulky commercial transducers are employed to generate acoustic waves, it conflicts with miniaturization and integration efforts. To alleviate these shortcomings, surface acoustic wave (SAW) based techniques have been investigated owing to their low propagation loss, high sensitivity to the surface modification, low power consumption, and facile integration into microfluidic networks. One concern about the acoustic based separation technology is that the mechanical forces generated by the acoustic waves may potentially damage cells. However, since the operating frequencies of SAW separation devices (tens of MHz) correspond to time scales smaller than the molecular relaxation time and certainly any relaxation time of the cellular structures, there is no shear damage with these high frequency devices [31,32].

SAW devices have been investigated in wide variety of applications including fluid-mixing [33,34], fluid-pumping [35,36], particle focusing [30,37], and particle sorting/collection [38,39] in microchannels. Recently, standing surface acoustic waves (SSAW), generated by interdigitated microelectrodes on a piezoelectric substrate, have been demonstrated to separate polystyrene microparticles [40]. The technique of using SSAWs that travel along the substrate surface works with any microchannel material and can be incorporated easily into a multi-functional device design due to its simplicity. However, current state-of-the-art SSAW based particle separation platform employs two external sheath flows to divide particle mixture streams as well as to prevent trapping and aggregating along the sidewall of the channel [40]. Introducing sheath flow to a microchannel has several fundamental disadvantages, such as dilution of the analyte by the sheath liquid, need for accurate flow control between sample and sheath flow, complicated structure in order to create sheath flow, and separation efficiency strongly depending on the sheath liquid composition [41]. Previous studies have investigated sheathless 3D particle focusing [37] and pattering acting as acoustic tweezers [42] using SSAW without any particle/cell separation capability. Most recently, Nam et al. [43] has demonstrated a size-dependent particle separation using SSAW. However, the device still uses two sheath flows to align particles toward the central region of the microfluidic channel. As a result, currently there is no report of SSAW based particle separation technique without using any external sheath flow. In this Example, we present a sheathless SSAW based particle separation technique in a microfluidic channel. Using a novel two-stage design, the microparticles are continuously separated at the outlet without using an external sheath flow.

Discussion:

FIG. 2.1 shows the design concept and working mechanism of the two-stage SSAW particle separator. The first stage uses a relatively narrow channel to align particles at the center of the microfluidic channel without introducing any external sheath flow. Two identical interdigitated transducers (IDTs) are fabricated on a piezoelectric substrate, and a microfluidic channel is aligned between the IDTs. When the two IDTs are stimulated with RF signals of equal amplitude, two series of surface acoustic waves propagate in opposite directions toward the particle solution inside the microchannel. The interference of the two surface acoustic waves forms a SSAW that generates a periodic distribution of pressure nodes and anti-nodes inside the microchannel. When the surface acoustic waves reach the liquid medium inside the microchannel, they are converted to leakage waves resulting in pressure fluctuations in the medium. The acoustic radiation forces caused by the pressure fluctuations move the particles toward the pressure nodes in the SSAW field. In the first stage, the width of the microchannel ($W_1$) is chosen to be the half-wavelength ($\lambda_1/2$) of the SSAW so that the channel contains only one pressure node located in the center of the channel (FIG. 2.1). Thus, particles will aggregate at the center-line of the microchannel by the time they reach the end of the first stage microchannel. In the second stage, a wider channel ($W_2$) that has a width of one-wavelength of the SSAW ($\lambda_2$), so that two off-center pressure nodes exist in the channel. Suspended particles enter the second stage channel at the anti-node. Thus the acoustic forces will move particles towards the pressure nodes. Because the acoustic force on a particle is proportional to its volume, large particles will move to the pressure nodes more quickly than small particles during a given short SSAW exposure time. Therefore the particles can be separated by size.

FIG. 2.1 illustrates the conceptual view of the sheathless particle separator using standing surface acoustic waves. The first stage aligns the particles on the center line, while the second stage separates them according to size. A particle in an SSAW field is subjected to an acoustic radiation force, which can be expressed as [44]:

$$F_r = -\frac{(\pi p_o^2 V \beta_m)}{2\lambda} \phi(\beta, \rho) \sin(2kx) \quad (1)$$

$$\phi(\beta, \rho) = \frac{(5\rho_p - 2\rho_m)}{(2\rho_p + \rho_m)} - \frac{\beta_p}{\beta_m} \quad (2)$$

where, $p_o$, V, $\lambda$, $\beta$, $\rho$, k, x are the acoustic pressure amplitude, particle volume, wavelength, compressibility, density, wave number, and the distance from the pressure node respectively. The subscripts of p and m denote particle and liquid medium, respectively. Acoustic contrast factor (Ø) determines whether the particle will move towards the pressure node or the anti-node: if Ø>0, particles will be attracted to the pressure node; if Ø<0, particles will aggregate at the anti-node. In general, most solid particles including cells in liquid medium move towards pressure node [45]. FIG. 3.1 shows the acoustic radiation force distribution as a function of particle size in the microchannel of the second stage. The acoustic radiation forces were represented by Equations (1) and (2) under the presented experiment conditions ($\rho$=1.05 g/cm$_3$ and $\beta$=2.46e−10 Pa$_{-1}$ for polystyrene particles, $\rho$=1.0 g/cm$_3$ and $\beta$=4.58e−10 Pa$_{-1}$ for DI-water medium, wavelength=300 μm, input power=0.5 W). The results show that the acoustic forces change sinusoidally and are equal to zero at the wave crest, wave trough and nodal plane. Especially, as the particle diameter is reduced, the acoustic force decreases very rapidly. The peak value of the acoustic force of 10 μm particle is 191 pN, while that of 3 μm particle is only 5 pN. Since the particle displacements induced by acoustic forces are strongly dependent on the particle size, the larger particles are moved to the pressure nodes, whereas smaller particles remain in the center stream at a given SAW working time. It is important to note that our approach is capable of particle separation based on not only size, but also by density, compressibility, or acoustic contrast factor.

The particles or cells suspended in a medium are subjected to four different forces: acoustic radiation force, viscous drag force, gravity force, and buoyant force. FIG. 3.2 illustrates theoretically calculated magnitude of these forces as a function of particle size at the present experimental parameters ($\rho$=1.05 g/cm$_3$ and $\beta$=2.46e−10 Pa$_{-1}$ for polystyrene particles, $\rho$=1.0 g/cm$_3$ and $\beta$=4.58e−10 Pa$_{-1}$ for DI-water medium, wavelength=300 μm, input power=0.5 W). It can be observed that the gravitational and buoyant forces are balanced with similar magnitudes and opposite directions. Since the viscous force is proportional to the radius of the particles (r) while the acoustic force is proportional to the volume ($r_3$) of the particles, the acoustic forces are generally dominant in the case of larger particles. However, when the diameter of the particles is less than about 0.3 μm, the acoustic forces are smaller than the viscous forces. In this case, the size-dependant separation may not be achieved by acoustic radiation forces. The time required for the particle migration toward the pressure node can be theoretically predicted by a quantitative force analysis [40,42]. FIG. 3.3 shows the time required for the particle migration toward the pressure node with varying the diameters of the particles. As expected, the larger particle moves to the pressure node faster than the smaller particle (for instance, 3 μm: 1.81 s, 5 μm: 0.65 s, 10 μm: 0.16 s). Based on these predictions, the length of the microchannel in each stage can be determined. The channel length of the first stage should be long enough so that all particles can reach the pressure node at the center of the channel, while the channel length of the second stage should be relatively short so that only larger particle move to the pressure nodes. It is important to note that the actual migration time of the particles toward the pressure node can also be readily adjusted by tuning the input power and flow rate during the experiments.

Device Design and Fabrication:

As presented in Table 1, the SAW wavelength, the IDT finger pitch, and finger width were chosen as 300 μm, 300 μm, and 75 μm, respectively. The channel width of the first stage was 150 μm, half of the SAW wavelength, to contain only one pressure node in the center of the channel. On the other hand, the second stage width was 300 μm, the same as SAW wavelength, to have two pressure nodes in the channel. The resonance frequency of the SAW is determined by the ratio of the SAW velocity ($V_{SAW}$) on the substrate and SAW wavelength (λ); $f=V_{SAW}/\lambda$. With the SAW velocity 3,990 m/s for the chosen SAW direction on the substrate, the resonance frequency is 13.2 MHz.

TABLE 1

Design parameters used for the size-based separation experiments.

| Wavelength (λ) | 300 μm | First channel width | 150 μm |
|---|---|---|---|
| IDT finger width | 75 μm | Second channel width | 300 μm |
| IDT finger pitch | 150 μm | Channel height | 100 μm |
| IDT finger pairs | 20 pairs | Resonance frequency | 13.2 MHz |

Nam et al. have also reported that the pressure nodes would appear in the two-dimensional plane along the axial flow in a microchannel as the direction of SSAW is perpendicular to the axial flow direction [43]. Such two-dimensional particle distribution would be dependent on the channel height or aspect ratio of channel. For a channel with low aspect ratio, the flow velocity is practically uniform over the channel width except near the edges, while having a parabolic profile over the shorter dimension [46]. Thus, thin rectangular channel would be more efficient for applying SSAWs on particles. As a result, the microchannel height is chosen as 100 μm ensuring a low aspect ratio (1st stage: H/W=0.66, 2nd stage: H/W=0.33) for increased separation efficiency.

The sheathless acoustic particle separator was realized by three consecutive fabrication steps: the fabrication of IDTs on a substrate, the fabrication of the PDMS microchannel, and the bonding of the PDMS microchannel to the substrate containing IDTs. FIG. 2.4 shows the fabrication process flow of the present sheathless acoustic particle separator. For the fabrication of the IDT substrate, a two-side polished Y+128° X-propagation lithium niobate ($LiNbO_3$) wafer was used, as it has a high electromechanical coupling coefficient [47]. The wafer was first pre-cleaned by rinsing with acetone, methanol and de-ionized water. A 100 nm thick chrome layer was then deposited on the lithium niobate wafer using CRC sputtering system (Torr International, New Windsor, N.Y., USA). The lithium niobate wafer was then spun with 1.6 μm-thick photoresist (S1813, Shipley, Marlborough, Mass., USA) at 3,000 rpm for 40 s, and soft baking of the photoresist was performed on a hot plate at 100° C. for 1 min. The wafer was patterned with a UV light source with an exposure dose of 125 mJ/$cm_2$ and developed in a photoresist developer (MF 319, Shipley) for 70 s. After hard baking was performed on a hot plate at 115° C. for 5 min, the chrome layer was etched using chrome etchant (CR-7S, Cyantek, Fremont, Calif., USA). Finally, the photoresist was removed by the photoresist remover. Each IDT includes 20 finger pairs with 150 μm finger pitch and 75 μm finger width. The sizes of IDT regions fabricated on the first stage and the second stage are 7.7 mm×6 mm and 1.7 mm×6 mm, respectively. The fabricated IDTs on the lithium niobate substrate are shown in FIG. 2.5(a).

The microchannel was fabricated with a PDMS micromolding technique. To obtain 100 μm thick mold layer, negative photoresist (SU-8 2075, MicroChem, Newton, Mass., USA) was spun onto the silicon wafer at 500 rpm for 10 s with acceleration of 100 rpm/s to spread out the photoresist, then at 2,000 rpm for 30 s with acceleration of 300 rpm/s. The wafer was then soft baked for 5 min at 65° C. and 20 min at 95° C. The wafer was then patterned with a UV light source with an exposure dose of 240 mJ/$cm^2$ and post exposure baking was performed directly after exposure for 5 min at 65° C. and 10 min at 95° C. After developed in the SU-8 developer for 10 min, the wafer was hard baked for 5 min at 150° C. The uniformity of the SU-8 mold height was confirmed using a surface profilometer. The PDMS oligomer and crosslinking prepolymer of the PDMS agent from a Sylgard™ 184 kit (Dow Corning, Midland, Mich., USA) was mixed in a weight ratio of 10:1, poured onto the SU-8 mold, and then cured at room temperature for 24 h to prevent PDMS shrinking due to heat. After the PDMS replica was peeled off from the mold, the inlets and outlets were generated using 20-gauge needle. The fabricated microchannel mold is shown in FIG. 2.6(b). For bonding the PDMS microchannel to the substrate containing IDTs, oxygen plasma (1 min at 20 sccm oxygen flow rate, 500 mTorr chamber pressure, and 100 W power) was used to activate both surfaces. After ethanol, acting as a lubricant, was dropped on the surface of IDT substrate, alignment of the PDMS microchannel and IDT substrate was conducted. FIG. 2.6(c) shows a complete sheathless acoustic particle separator including the PDMS microchannel and IDT substrate.

Experimental Set-up

An experiment was conducted with the device on an inverted microscope (IX-51, Olympus). A mixture solution of polystyrene fluorescent particles (Thermo Scientific, Waltham, Mass., USA) with diameters of 3 μm and 10 μm diameter (ρ=1.05 g/$cm_3$ and β=2.46e−10 $Pa_{-1}$ for polystyrene particles, ρ=1.0 g/$cm_3$ and β=4.58e−10 $Pa_{-1}$ for DI-water medium) was injected into the microchannel by a syringe pump (KDS200, KD Scientific, Holliston, Mass., USA). Also, for high resolution particle separation experiments, a mixture solution of polystyrene fluorescent particles with diameters of 3 μm (red) and 5 μm (green)

diameters was used. An AC signal was generated by a signal generator (AFG3022B, Tektronix) and then amplified by an RF power amplifier (325LA, ENI). The signal was split two ways to provide identical signals to the IDTs and generate SSAW. The high speed images of fluorescent in the microchannel were obtained with a CCD camera (XM-10, Olympus) and image acquisition software (cellSens, Olympus). A complete experimental setup is shown in FIG. 3.4.

To study the effect various parameters on the separation efficiency, the input power range applied to the IDTs was from 250 mW to 1 W, the flow rate ranged from 0.5 µL/min to 5 µL/min, and the concentration of each of the particles in the sample suspension ranged from 1% to 4% by volume. The PDMS microchannel was responsible for the range of the power applied in the present experiments. The net power applied to the IDTs to achieve particle focusing and separation depends on the SAW wavelength, particle size, and flow speed. Prior studies of SAW induced by IDT have applied similar power values to PDMS microchannel for particle manipulation [23,32,43].

Results and Discussion:

At three different locations marked as (I), (II) and (III) in FIG. 3.5(*a*), the distribution of 3 µm and 10 µm PS particle streams was captured during the separation process as shown in FIG. 3.5(*b*). During the experiment, the frequency, the input power, the flow rate, and the concentration were set to 13.2 MHz, 1 W, 0.5 µL/min, and 1% by volume, respectively. Location (I) was before the particles entered the first stage. One can clearly observe that both sizes of particles were randomly scattered in the channel. When particles entered the first stage (location (II)), the acoustic forces acting on the particles aligned them at the center of the channel where pressure nodes existed. Location (III) coincided with the second stage of the device. As can be observed from the figure of the location (III), the 10 µm particles moved to the pressure nodes while the 3 µm particles remained in the center of the channel because the acoustic forces exerted on the 3 µm particles were insufficient to push them into the pressure nodes during a given short SSAW exposure time. As a result, the larger particles were separated to the side channels and the smaller particles were directed to the center channel. FIG. 3.5(*c*) shows the distribution of 3 µm and 5 µm polystyrene particle streams during the separation process at the same locations as illustrated in FIG. 3.5(*a*). Since the acoustic forces were not applied to the inlet region, expectedly both particle sizes were randomly distributed in the channel (location (I)). As the particles entered the first stage, they were accumulated and aligned by the acoustic forces to the center of the channel where the pressure node existed (location (II)). When the particles traveled to the second stage (location (III)), 5 µm particles did not migrate completely to the pressure nodes located near side walls and remained in the center stream due to insufficient acoustic forces during short SSAW exposure time. On the other hand, when the input power was significantly increased even 3 µm particles are driven to the pressure nodes, conflicting with our separation efforts. As a result, an optimization study has been conducted to determine the appropriate input power and the flow rate parameters to accomplish high-resolution separation with small size difference particle streams. As illustrated in FIG. 3.5(*c*) location III, with the optimized input power parameter of 1.45 W and flow rate of 0.2 µL/min, 5 µm particles were separated to the side channels while 3 µm particles were collected to the center channel. These experiments show that the present device is capable of separating different-size particles without introducing any external sheath flow to the microchannel. To quantitatively determine the separation efficiency, the images were acquired from each outlet at 20 frames per second using CCD camera. The acquired images (600 frames) were analyzed with image processing software (ImageJ®, National Institutes of Health, Bethesda, Md., USA) to count the number of particles collected from each outlet. First, the images were converted to grayscale and then the threshold was set for each image. The thresholded images were then converted to binary images. Since some of particles were agglomerated, automatic thresholding method recognized them as a single object. Thus, a watershed segmentation process was performed to accurately count such cases. Finally, the number of particles was quantified using the menu command Analyze particles with the specific parameters. FIG. 3.6 shows the percentage of each of the two size particles collected from each outlet. The graph demonstrates that all 10 µm particles (100%) were separated to the side outlets, while most 3 µm particles (94.8%) remained in the center channel.

As a result of the particle counting analysis, the separation efficiency for both particle sizes as a function of power applied to IDTs is shown in FIG. 3.7. The driving frequency was 13.2 MHz, the particle concentration was 1% by volume, and the flow rate was fixed at 0.5 µL/min. As can be observed from this figure, the separation efficiency of the 3 µm and the 10 µm particles were measured in the range of 89.5-94.8% and 93.7-100%, respectively, at the applied power range of 0.25 to 1 W.

The separation efficiency increased as the input power increased because the acoustic radiation force is proportional to the acoustic pressure amplitude which is determined by the input power and acoustic impedance. The effect of the flow rate on the particle separation efficiency is also investigated in FIG. 3.8. The driving frequency, particle concentration, and the applied power were kept constant at 13.2 MHz, 1% by volume, and 1 W, respectively. The separation efficiencies of the 3 µm and the 10 µm particles were obtained in the range of 84.6-94.8% and 91.7-100%, respectively, at the flow rate range of 0.5 to 5 µL/min. The results show that lower flow rates provide higher separation efficiency since the particles were exposed to the SSAW field for a longer time period allowing higher number of particles moving to the pressure nodes.

Experimental efficiency results with different particle concentrations were also shown in FIG. 3.9. Constant driving frequency of 13.2 MHz, input power of 1 W, and a flow rate of 0.5 µL/min were used during these experiments. The separation efficiencies of the 3 µm and the 10 µm particles were achieved in the range of 87.4-94.8% and 94.6-100%, respectively, at the particle concentration range of 1 to 4%. The higher particle concentration yielded lower separation efficiency because the width of the aligned particles band at the first stage increased and existence of the thicker 3 µm particle band slowed down the displacement of the 10 µm particles across the microchannel in the second stage. As a result, the separation of very high concentration bioparticles such as whole blood with this platform may be more involved and may require additional power input or lower flow rate with the wider channel outlets to achieve high separation efficiency.

As expected, the separation efficiency of the 3 µm particles was lower than that of the 10 µm particles for all cases. The fundamental reason for this behavior was that the number of the misaligned 3 µm particles at the first stage was more than that of the 10 µm particles due to the relatively low acoustic forces exerted on the 3 µm particles. In the separation procedure of this platform, the alignment of the particle is one of the most important tasks directly affecting the efficiency of the separation. If the particles don't line up at the center of the channel before entering the second stage, this can negatively impact the separation efficiency, as illustrated by our own experiments. It is worth commenting here that this particular design is only capable of separating two different size particle streams. However, as shown in FIG. 3.1, the peak values of the acoustic force on 3 µm, 5 µm, 7 µm, and 10 µm particles are 5 pN, 24 pN, 66 pN, and 191 pN, respectively. This force magnitude difference is sufficient to achieve three or more different size particle separation. Hence by modifying the working wavelength, the IDT configuration, the width of the channel, and the number of the channel outlets separation of three or more different size particle streams can be achieved with this platform. It is important to note that this particle separator is ideal for the microparticle sensor because (1) it is applicable to all types of solid particles regardless of their size, shape, and electrical/magnetic/optical properties; (2) it is a non-invasive method and requires low power intensity; (3) it allows the use of a relatively large microfluidic channel in comparison to particle separation using pinched flow fractionation [6,11,48] and deterministic lateral displacement [49-51], which will allow for high throughput and cause less problems with clogging, and most importantly; (4) it does not require the use of sheath flow, which usually change the composition and concentration of the analyte.

Conclusion:

In summary, sheathless SSAW based particle separation using a novel two-stage microfluidic platform has been demonstrated. Two polystyrene fluorescent particles with different diameters (3 and 10 µm) were successfully separated with high efficiency. The prominent feature of the present microfluidic platform is that the device does not require the use of the sheath flow for positioning and aligning of particles in order to separate particles. The sheathless flow focusing and separation are integrated within a single microfluidic device and accomplished simultaneously. This device sets the first demonstration of SSAW based separation in a microfluidic channel to eliminate sheath flows. We anticipate that this sheathless acoustic particle separation method will find broad applications in wide variety of biological and biomedical applications.

References, each of which is incorporated herein by reference:

1. Moon, S.; Gurkan, U. A.; Blander, J.; Fawzi, W. W.; Aboud, S.; Mugusi, F.; Kuritzkes, D. R.; Demirci, U. Enumeration of CD4(+) T-cells using a portable microchip count platform in tanzanian HIV-infected patients. *PLoS One* 2011, doi: 10.1371/journal.pone.0021409.
2. Gascoyne, P.; Satayavivad, J.; Ruchirawat, M. Microfluidic approaches to malaria detection. *Acta Trop.* 2004, 89, 357-369.
3. Jagtiani, A. V.; Carletta, J.; Zhe, J. A microfluidic multichannel resistive pulse sensor using frequency division multiplexing for high throughput counting of micro particles. *J. Micromech. Microeng.* 2011, 21, 065004:1-065004:10.
4. Zhe, J.; Jagtiani, A.; Dutta, P.; Hu, J.; Carletta, J. A micromachined high throughput coulter counter for bioparticle detection and counting. *J. Micromech. Microeng.* 2007, 17, 304-313.
5. Du, L.; Zhe, J. A.; Carletta, J.; Veillette, R.; Choy, F. Real-time monitoring of wear debris in lubrication oil using a microfluidic inductive Coulter counting device. *Microfluid. Nanofluid.* 2010, 9, 1241-1245.
6. Yamada, M.; Seki, M. Hydrodynamic filtration for on-chip particle concentration and classification utilizing microfluidics. *Lab Chip* 2005, 5, 1233-1239.
7. Yamada, M.; Kano, K.; Tsuda, Y.; Kobayashi, J.; Yamato, M.; Seki, M.; Okano, T. Microfluidic devices for size-dependent separation of liver cells. *Biomed. Microdevices* 2007, 9, 637-645.
8. Huang, L. R.; Cox, E. C.; Austin, R. H.; Sturm, J. C. Continuous particle separation through deterministic lateral displacement. *Science* 2004, 304, 987-990.
9. Long, B. R.; Heller, M.; Beech, J. P.; Linke, H.; Bruus, H.; Tegenfeldt, J. O.
Multidirectional sorting modes in deterministic lateral displacement devices. *Phys. Rev. E* 2008, 78, 046304.
10. Larsen, A. V.; Poulsen, L.; Birgens, H.; Dufva, M.; Kristensen, A. Pinched flow fractionation devices for detection of single nucleotide polymorphisms. *Lab Chip* 2008, 8, 818-821. Sensors 2012, 12 920
11. Yamada, M.; Nakashima, M.; Seki, M. Pinched flow fractionation: Continuous size separation of particles utilizing a laminar flow profile in a pinched microchannel. *Anal. Chem.* 2004, 76, 5465-5471.
12. Huh, D.; Bahng, J. H.; Ling, Y. B.; Wei, H. H.; Kripfgans, O. D.; Fowlkes, J. B.; Grotberg, J. B.; Takayama, S. Gravity-driven microfluidic particle sorting device with hydrodynamic separation amplification. *Anal. Chem.* 2007, 79, 1369-1376.
13. Di Carlo, D. Inertial microfluidics. *Lab Chip* 2009, 9, 3038-3046.
14. Kuntaegowdanahalli, S. S.; Bhagat, A. A. S.; Kumar, G.; Papautsky, I. Inertial microfluidics for continuous particle separation in spiral microchannels. *Lab Chip* 2009, 9, 2973-2980.
15. Jung, J.; Han, K. H. Lateral-driven continuous magnetophoretic separation of blood cells. *Appl. Phys. Lett.* 2008, 93, 223902.
16. Han, K. H.; Frazier, A. B. Paramagnetic capture mode magnetophoretic microseparator for high efficiency blood cell separations. *Lab Chip* 2006, 6, 265-273.
17. Zhu, T. T.; Marrero, F.; Mao, L. D. Continuous separation of non-magnetic particles inside ferrofluids. *Microfluid. Nanofluid.* 2010, 9, 1003-1009.
18. Kose, A. R.; Koser, H. Ferrofluid mediated nanocytometry. Lab Chip 2012, 12, 190-196. 19. Shah, G. J.; Ohta, A. T.; Chiou, E. P. Y.; Wu, M. C.; Kim, C. J. EWOD-driven droplet microfluidic device integrated with optoelectronic tweezers as an automated platform for cellular isolation and analysis. *Lab Chip* 2009, 9, 1732-1739.
20. MacDonald, M. P.; Spalding, G. C.; Dholakia, K. Microfluidic sorting in an optical lattice. *Nature* 2003, 426, 421-424.
21. Chen, D. F.; Du, H.; Li, W. H. A 3D paired microelectrode array for accumulation and separation of microparticles. *J. Micromech. Microeng.* 2006, 16, 1162-1169.
22. Gascoyne, P. R. C.; Vykoukal, J. Particle separation by dielectrophoresis. *Electrophoresis* 2002, 23, 1973-1983.
23. Tan, M. K.; Tjeung, R.; Ervin, H.; Yeo, L. Y.; Friend, J. Double aperture focusing transducer for controlling microparticle motions in trapezoidal microchannels with surface acoustic waves. *Appl. Phys. Lett.* 2009, 95, 134101.
24. Kapishnikov, S.; Kantsler, V.; Steinberg, V. Continuous particle size separation and size sorting using ultrasound in a microchannel. *J. Stat. Mech.* 2006, doi: 10.1088/1742-5468/2006/01/P01012.

25. Nilsson, A.; Petersson, F.; Jonsson, H.; Laurell, T. Acoustic control of suspended particles in micro fluidic chips. *Lab Chip* 2004, 4, 131-135.
26. Wiklund, M.; Gunther, C.; Lemor, R.; Jager, M.; Fuhr, G.; Hertz, H. M. Ultrasonic standing wave manipulation technology integrated into a dielectrophoretic chip. *Lab Chip* 2006, 6, 1537-1544.
27. Demirci, U.; Montesano, G. Single cell epitaxy by acoustic picoliter droplets. *Lab Chip* 2007, 7, 1139-1145.
28. Friend, J.; Yeo, L. Y. Microscale acoustofluidics: Microfluidics driven via acoustics and ultrasonics. *Rev. Mod. Phys.* 2011, 83, 647-704.
29. Jonsson, H.; Holm, C.; Nilsson, A.; Petersson, F.; Johnsson, P.; Laurell, T. Particle separation using ultrasound can radically reduce embolic load to brain after cardiac surgery. *Ann. Thorac. Surg.* 2004, 78, 1572-1578.
30. Li, P. C. H.; Wang, W. J.; Parameswaran, M. An acoustic wave sensor incorporated with a microfluidic chip for analyzing muscle cell contraction. *Analyst* 2003, 128, 225-231.
31. Peterson, F.; Aberg, L.; Sward-Nilsson, A. M.; Laurell, T. Free flow acoustophoresis: Microfluidic-based mode of particle and cell separation. *Anal. Chem.* 2007, 79, 5117-5123.
32. Shi, J. J.; Mao, X. L.; Ahmed, D.; Colletti, A.; Huang, T. J. Focusing microparticles in a microfluidic channel with standing surface acoustic waves (SSAW). *Lab Chip* 2008, 8, 221-223.
33. Tan, M. K.; Yeo, L. Y.; Friend, J. R. Rapid fluid flow and mixing induced in microchannels using surface acoustic waves. *Europhys. Lett.* 2009, 87, 47003.
34. Tseng, W. K.; Lin, J. L.; Sung, W. C.; Chen, S. H.; Lee, G. B. Active micro-mixers using surface acoustic waves on Y-cut 128 degrees $LiNbO_3$. *J. Micromech. Microeng.* 2006, 16, 539-548.
35. Cecchini, M.; Girardo, S.; Pisignano, D.; Cingolani, R.; Beltram, F. Acoustic-counterflow microfluidics by surface acoustic waves. *Appl. Phys. Lett.* 2008, 92, 104103.
36. Girardo, S.; Cecchini, M.; Beltram, F.; Cingolani, R.; Pisignano, D. Polydimethylsiloxane-LiNbO3 surface acoustic wave micropump devices for fluid control into microchannels. *Lab Chip* 2008, 8, 1557-1563.
37. Shi, J. J.; Yazdi, S.; Lin, S. C. S.; Ding, X. Y.; Chiang, I. K.; Sharp, K.; Huang, T. J. Three-dimensional continuous particle focusing in a microfluidic channel via standing surface acoustic waves (SSAW). *Lab Chip* 2011, 11, 2319-2324.
38. Franke, T.; Braunmuller, S.; Schmid, L.; Wixforth, A.; Weitz, D. A. Surface acoustic wave actuated cell sorting (SAWACS). *Lab Chip* 2010, 10, 789-794.
39. Tan, M. K.; Yeo, L. Y.; Friend, J. R. Unique flow transitions and particle collection switching phenomena in a microchannel induced by surface acoustic waves. *Appl. Phys. Lett.* 2010, 97, 234106:1-234106:3.
40. Shi, J. J.; Huang, H.; Stratton, Z.; Huang, Y. P.; Huang, T. J. Continuous particle separation in a microfluidic channel via standing surface acoustic waves (SSAW). *Lab Chip* 2009, 9, 3354-3359.
41. Strege, M. A.; Lagu, A. L. *Capillary Electrophoresis of Proteins and Peptides*; Humana Press: Totowa, N. J., USA, 2004.
42. Shi, J. J.; Ahmed, D.; Mao, X.; Lin, S. C. S.; Lawit, A.; Huang, T. J. Acoustic tweezers: Patterning cells and microparticles using standing surface acoustic waves (SSAW). *Lab Chip* 2009, 9, 2890-2895.
43. Nam, J.; Lee, Y.; Shin, S. Size-dependent microparticles separation through standing surface acoustic waves. *Microfluid. Nanofluid.* 2011, 11, 317-326.
44. Yosioka, K.; Kawasima, Y. Acoustic radiation pressure on a compressible sphere. *Acustica* 1955, 5, 167-173.
45. Laurell, T.; Petersson, F.; Nilsson, A. Chip integrated strategies for acoustic separation and manipulation of cells and particles. *Chem. Soc. Rev.* 2007, 36,492-506.
46. Stiles, T.; Fallon, R.; Vestad, T.; Oakey, J.; Marr, D. W. M.; Squier, J.; Jimenez, R. Hydrodynamic focusing for vacuum-pumped microfluidics. *Microfluid. Nanofluid.* 2005, 1, 280-283.
47. Gardner, J. W.; Varadan, V. K.; Awadelkarim, O. O. *Microsensors, MEMS, and Smart Devices*; John Wiley & Sons: Hoboken, N.J., USA, 2001.
48. Yang, S.; Undar, A.; Zahn, J. D. A microfluidic device for continuous, real time blood plasma separation. *Lab Chip* 2006, 6,871-880. Sensors 2012, 12 922
49. Morton, K. J.; Loutherback, K.; Inglis, D. W.; Tsui, O. K.; Sturm, J. C.; Chou, S. Y.; Austin, R. H. Hydrodynamic metamaterials: Microfabricated arrays to steer, refract, and focus streams of biomaterials. *Proc. Natl. Acad. Sci. USA* 2008, 105, 7434-7438.
50. Inglis, D. W.; Davis, J. A.; Austin, R. H.; Sturm, J. C. Critical particle size for fractionation by deterministic lateral displacement. *Lab Chip* 2006, 6,655-658.
51. Inglis, D. W. Efficient microfluidic particle separation arrays. *Appl. Phys. Lett.* 2009, 94, 013510:1-013510:3.

EXAMPLE 3

Brief Introduction:

A goal of this Example to develop a miniaturized microfluidic sensor for realtime condition monitoring of rotating and reciprocating machinery that detects metal wear debris in the machinery's lubrication oil. The use of standing surface acoustic waves to separate particles by size allows each debris particle to be delivered to an appropriately sized detector, significantly improving the detection limit. The use of a parallel array of inductive Coulter counting detectors whose output signals are multiplexed enables rapid analysis of a large volume of lubricants, greatly improving the throughput of the sensor, without requiring separate measurement of each detector. In this Example, we propose to 1) develop a standing surface acoustic wave (SSAW) particle separator that separates metal debris particles in lubrication oil according to their size, 2) develop a multiplexed multi-channel detector array for metal particles using an inductive Coulter counting principle, 3) develop a micromachining process that enables fabrication of both components and detection electronics on a compact miniature lab-on-a-chip device, and 4) demonstrate the utility of the sensor for real-time detection and quantification of debris particles in lubrication oil.

A successfully developed sensor can have broad impact on the transportation, manufacturing and military industries. The sensor can facilitate better maintenance scheduling, thereby significantly reducing the cost of machine operation. The high throughput, sensitivity and dynamic range of the instrumentation, along with its low cost, may make it an ideal instrument for real-time condition monitoring and life prognosis for a variety of machinery including bearings, gearboxes, and turbomachinery. It is a powerful complement to existing offline oil wear debris analysis. Experimental and theoretical studies of SSAW particle focusing and separation in microchannels are particularly important in advancing the state-of-the-art in particle manipulation for lab-on-a-chip devices. The studies may provide a generalized methodology for particle separation for a broad variety of particles and media. The proposed research, aiming at fundamental understanding of inductive Coulter counting principles using planar detectors, may form the scientific foundation for the development of advanced sensors systems for micro/nanoscale particle sensing. In particular, studies of particle manipulation and sensing in a nonconductive, high viscous environment are poised to have a transformative impact on new soft materials processing involving micro/nano particles, and the development of microsensors for detecting metal particle contamination in nonconductive materials and environments.

Introduction:

Condition monitoring has become essential in maintaining and extending the health of high-speed rotating and reciprocating machinery used in today's transportation, manufacturing and defense industries. One of the most important objectives for these industries is to minimize production costs. At present, maintenance and down time costs in some heavy manufacturing industries, for example, can be as high as 50% of the total operating costs. Accurate condition monitoring methodologies are being sought to facilitate the effective scheduling of maintenance and repair downtime, and, particularly in the air transport industries, to ensure the safety of longrange operations. Although vibration analysis has been extensively used in condition monitoring of rotating machinery [1], the analysis of continuous in-situ vibration data requires sophisticated data acquisition and computational procedures; these procedures are difficult to implement, and, at times, machine faults cannot be accurately detected [2]. An effective alternative approach is to detect signs of potential machine failure by examining the life blood of a rotating or reciprocating machine: its lubrication oil. Examination of lubrication oil has shown a direct relationship between the size and concentration of debris particles in the oil and the level of wear in the machinery components. During normal machine operation, the concentration of wear debris particles is low, and usually particles are in the range of 1 to 10 microns in size. When abnormal wear begins, larger particles are seen, in the range of 10 to 50 microns [3]. The concentration and size of particles increase gradually with time, even after the working fluid is changed, until the machine fails. Furthermore, today's tribological surfaces are often coated with special non-ferrous linings that reduce contact friction. Thus, the ability to differentiate ferrous and non-ferrous debris can provide valuable information that will help in identifying and locating worn components. In the last several decades, offline lubrication oil analysis methods, including spectroscopy [4-8] and ferrography [9-11], have been applied as powerful tools to determine optimal maintenance/repair intervals and to predict impending mechanical failure. Although the laboratory analysis used for these methods provides comprehensive and detailed information about the wear debris particles, the test procedures are time consuming, and often require complicated setup and skilled analysts. Even more importantly, the methods do not provide the real-time information about machine health that is needed to detect the need for emergency maintenance and repairs. For real-time diagnosis, online methods are required. In the last decade, a few online lubrication oil monitoring devices have been developed. Optical methods such as scattering counters [12-15] are capable of detecting particles in lubricant oil. However, the accuracy of the optical approach is affected by particle properties (refractive index, shape, etc), the clarity of the oil, and the existence of air bubbles. The acoustic emission detection method [16-19], based on the amplitude change of reflected acoustic waves, is often sensitive to interference caused by background acoustic emission and lubricant oil temperature variations. Bulk capacitance sensing [20-23] using a simple sensing structure can provide an overall measurement of bulk dielectric constant change due to presence of debris particles, but the results are often complicated by temperature variation and oil property degradation. In addition, the bulk measurement makes it difficult to accurately determine debris sizes and concentration. Even more importantly, none of these methods can differentiate ferrous and non-ferrous debris particles. Inductive debris sensors [24-27] have met some success in differentiating ferrous and non-ferrous particles, but so far have been used to detect only debris larger than 100 μm in size; thus, these devices are not sensitive enough to detect a problem before the onset of machine failure in many applications. In general, today's online debris monitoring devices can provide only limited information on the progression of machine wear and devices that provide more information do not have in situ online capability, and so cannot provide advance warning of sudden catastrophic failure.

In this Example we propose a miniature microfluidic sensor for real-time in situ condition monitoring of rotating and reciprocating machinery that uses an inductive Coulter counting principle to detect debris in lubrication oil. The sensor includes two major components as shown in FIG. 4.1: 1) a particle separator that uses standing surface acoustic waves to separate debris particles by size, and 2) an array of detection sensors, working in parallel on the streams of separated particles, and detecting each particle individually as it passes a sensing coil. This new sensor will combine technologies in microfluidics, MEMS, sensors and instrumentation, multiplexing, and signal processing. Because the particles are separated by size, it is possible to size a particular particle detector, which includes a microchannel with an embedded planar coil, for maximum sensitivity to particles of the size steered to it. This, the proposed device will be able to detect significantly smaller debris than existing magnetic debris sensors, which are limited to debris 100 μm or larger. From our preliminary work, we expect that the device will be able to detect debris about 10 μm in diameter, or even smaller. The use of an inductive Coulter counting principle enables the detection, counting and differentiation of ferrous and non-ferrous metal debris particles, because the method scans each particle as it is carried in the non-conductive lubrication oil past the coil. The use of parallel detection sensors allows a larger volume of lubricant sample to be analyzed in parallel, for high throughput; this will be accomplished by using signal multiplexing without having to monitor each channel individually.

Discussion:

An objective discussed in this Example include developing a high throughput microfluidic sensor that can rapidly detect and quantify metal debris particles in lubrication oil ranging in size from 10 μm to 100 μm, which are indicative of potential machine fault for rotating mechanical machinery. The sensor is expected to provide information on the size, shape, concentration, and composition of metal particles in the lubrication oil. Such information is critical for judging the health status of rotating machinery, and the proposed sensor will be suitable for integration into the mechanical system to provide the information without the need for shutdown or disassembly. One route of achieving this goal includes the following activities are proposed: (1) Develop a standing surface acoustic wave particle separator that separates suspended metal debris particles in lubrication oil according to their size. Separated particles are sent to corresponding detectors by size, greatly improving the detection limit. Interdigitated transducers will be used to generate standing surface acoustic waves (SSAW), which can be easily fabricated and integrated to a microfluidic device. The use of SSAW allows the use of a relatively large microfluidic channel during particle separation, permitting processing of large volume of lubricant samples and reducing the chance of clogging the microchannels. (2) Develop a multiplexed multichannel detection array for metal particle detection using inductive Coulter counting principle. The use of the inductive Coulter counting principle allows the sensor to "scan" each individual debris particle. The use of an array of parallel inductive Coulter counting detectors and signal multiplexing enables high throughput detection of metal debris particles, which is critical for high speed quantification of metal wear for real time condition monitoring. (3) Develop a micromachining process that enables fabrication of both components and detection electronics on a compact miniature lab-on-a-chip device. We will fabricate the particle separator, the particle detectors, and detection electronics on a compact lab-on-a-chip device that possesses the advantages of miniaturization, high throughput and low cost. (4) Demonstrate the utility of the sensor for high speed real time detection and quantification of metal debris particles in lubrication oil. The prototype sensor will be tested using standard aluminum and iron microparticles mixed with lubrication oil. Real time testing will be also conducted using a hydrodynamic bearing test rig.

Preliminary Results and Background:

Inductive Coulter Counting for Detection of Metal Particles:

The Coulter counting principle is an established technique to detect and count biological cells in an electrolyte solution [28-30]. A Coulter counter includes two reservoirs connected by a microchannel. Electrodes are used to monitor the resistance of the electrolyte in the microchannel. When an individual particle suspended in the solution passes through the microchannel, it displaces some of the electrolyte solution and causes a change in the electrical resistance of the microchannel measured at the electrodes. This approach is practical only when the microchannel contains electrolyte; however, because lubricant oil is non-conductive, the resistance change due to the passage of a particle is difficult to measure. To overcome this, we fabricated a microfluidic device to monitor the change in capacitance across a pair of microelectrodes in the microchannel [31, 32].

The schematic of the design is illustrated in FIG. 4.2($a$). When 10 to 25 μm metal particle passed through the microchannel, changes in the capacitance were detected (FIG. 4.2($b$)) owing to the difference in permittivity between the lubricant oil and the metal particle, and to the effect that the metal particle has on the electric field between the electrodes. While the device can detect very small metal particles (~10 μm), it was unable to differentiate ferrous and non-ferrous metal debris particles, which is important for condition monitoring for rotating machinery.

FIG. 4.3($a$) shows the schematics of the device that includes a mini-channel wounded by a solenoid. An AC voltage is applied across the solenoid, and induces a magnetic field in the solenoid (FIG. 4.3($b$)). The ideal source voltage is divided between the internal resistance of the voltage source and the impedance of the solenoid, so that the voltage across the solenoid (V1) depends on the solenoid's impedance. Any change in impedance of the solenoid induces a change in V1. If a ferrous but nonconductive particle (with relative magnetic permeability μr significantly higher than that of lubrication oil) is introduced into the microchannel, the magnetic flux is enhanced (FIG. 4.3($c$)), causing an increase in inductance Ls and an increase in V1. On the other hand, if a conductive but nonferrous particle is introduced into the microchannel, an eddy current is generated inside the metal particle in a way that opposes the original magnetic field (FIG. 4.3($d$)); as a result, the total magnetic flux is decreased, leading to a decrease in the inductance Ls and in the output voltage V1. The higher the frequency of the AC excitation, the larger the eddy current and therefore the larger the drop in the inductance Ls and in the output voltage V1. The two factors, magnetic permeability and eddy current, contribute to changes in Ls and in the output voltage V1 in competing ways if a particle is both ferrous and conductive. At high frequencies, the eddy current effect is dominant, and passage of a particle leads to an overall reduction in Ls and a negative voltage pulse. Therefore ferrous and non-ferrous conductive debris can be differentiated by looking at pulse polarity at an appropriate frequency. In our lab, mesoscale aluminum and steel particles passed through the microchannel vertically by force of gravity. The V1 was recorded for an excitation frequency of 100 kHz. The result is shown in FIG. 4.4. Ferrous particles generated positive inductance/voltage pulses, while non-ferrous particles generated negative pulses. This test indicates that the inductive Coulter counting device is able to distinguish the ferrous and non-ferrous particles and evaluate their sizes. We plan to minimize the device to microscale for detecting metal debris particles ranging from 10 μm to 100 μm.

Particle Separation in Microfluidics:

To date, various techniques for continuous microparticle separation have been studied, including optical separation [34-38], fluidic-only separation [39-41], and electric separation [42-44]. Of the optical separation methods, optical tweezers [45,46] require complex optical setup [47], and are not able to induce optical forces large enough to manipulate metal particles; fluorescence activated cell sorting (FACS) [48,49] is an established method to separate cells, but requires that particles be labeled with fluorescence. Fluidic-only separation techniques such as pinched flow fractionation [50-52] and deterministic lateral displacement (DLD) [53-55] have the advantage of not requiring any external force field. Pinched flow fractionation sorts particles by size in a pinched narrow segment comparable in size to the particles, and thus is low in throughput. Deterministic lateral displacement (DLD) separation also sorts particles exclusively by size, using only the geometries of microchannels. However, it has a high risk of clogging due to the high density post structures employed [56]. Of the electric separation methods, electrophoresis [57,58] is a well-known technique to separate micro/nanoscale particles, but works only for charged particles. Dielectrophoresis (DEP) separation [59-62] has received great attention in recent years due to its ability to manipulate polarizable particles in non-uniform electric fields [63]. However, only attractive (positive) DEP forces can be generated on metalparticles [64,65], so that metal particles travel towards the electrode surface. Because DEP forces increase exponentially as particles travel to the electrode surface [66], particles tend to become trapped on the electrodes. Suspended particles in a standing acoustic wave field are affected by acoustic forces. Acoustic waves generate pressure gradients in a liquid that can be used to manipulate or separate suspended particles [67-70]. Acoustic methods appear to be ideal particle manipulation methods for lab-on-a-chip devices because they are non-invasive and work for nearly any type of microscale particle. Recent studies [71-75] demonstrated the separation and manipulation of cells and particles in microfluidic channels, using a bulk acoustic wave (BAW) generated by substrate-bonded bulk transducers. However, the generation of bulk acoustic wave requires that the microchannel have excellent acoustic reflection properties [67]. As a result, a bulk acoustic wave is not a good choice for microfluidic devices made of materials with poor acoustic reflection, such as commonly used polydimethylsiloxane (PDMS). Additionally, it is difficult to integrate a bulk transducer into the proposed integrated microsystem. Recently, standing surface acoustic waves (SSAW), generated by interdigitated microelectrodes on a piezoelectric substrate, have been demonstrated to focus microparticles in microchannels [76]. FIG. 4.5 illustrates a SSAW focusing device and its working mechanism. Two interdigitated transducers (IDT) generate two series of surface acoustic waves that propagate in opposite directions. The two waves interfere and form the standing surface acoustic wave that generates periodic pressure nodes and anti-pressure nodes on the substrate.

Particles in the SSAW field are subjected to an acoustic radiation force [76]:

$$F_1 = -(\pi p_0^2 V_p \beta_m / 2\lambda) \cdot \phi \cdot \sin(4\pi x/\lambda) \quad (1)$$

where p0, $\lambda$, Vp, x and $\beta$m are the acoustic pressure, wavelength, particle volume, lateral position and compressibility of medium, respectively. An acoustic contrast factor $\phi$ determines the balanced position of particles: if $\phi>0$, particles will be pushed towards a pressure node (FIG. 4.5), and if $\phi<0$, particles will be pushed towards an anti-node [35-37, 40, 44]. Factor $\phi$ is defined by:

$$\phi = (5\rho_p - 2\rho_m)/(2\rho_p + \rho_m) - (\beta_p/\beta_m) \quad (2)$$

where $\rho$p, $\rho$m, $\beta$p are the particle density, medium density and particle compressibility, respectively. Metal particles, like most solid particles, typically have positive $\phi$ values. For example, our calculation shows that $\phi$ is 1.77, 2.27 and 2.24 for aluminum, copper and steel particles, respectively, in SAE 5W-30 lubrication oil. The fact that acoustic radiation force pushes metal particles towards a pressure node can be used to separate the particles by adjusting the positions of the pressure nodes. Compared to fluidic-only separation, SSAW separation permits the use of a relatively large microfluidic channel, allowing high throughput and causing less trouble with clogging. For these reasons, we propose to use standing surface acoustic waves for metal debris particle separation in lubrication oil.

Discussion:

This project proposes a miniature microfluidic device for condition monitoring of rotary and reciprocating machinery using detection of wear debris in lubrication oil. The illustration of the design concept is shown in FIG. 4.1. Metal particles suspended in lubrication oil are loaded into the device through an inlet. A standing surface acoustic wave will focus metal debris particles at the pressure node located at the center of the channel. This is necessary for the next-stage particle separation, which is sensitive to the initial positions of the particles. Next, a second standing surface wave is used to generate two pressure nodes off the channel's centerline. While all particles move towards one or the other of the pressure nodes, the larger particles are subjected to larger acoustic forces than the smaller particles, and so move more quickly; by careful design of the separator geometry and fluid flow rate, then, the particles can be separated by size. The streams of separated debris particles are guided to correspondingly sized detection sensors via separated microchannels. An array of inductive Coulter counting detectors, each include a microchannel and an embedded planar coil, are used to count and differentiate ferrous and non-ferrous metal debris particles, and evaluate their sizes and shapes. The detailed research plan will be described below.

Develop a SSAW Particle Separator

FIG. 4.6 illustrates the concept of the proposed standing surface acoustic wave (SSAW) particle separator. The particle separator includes two stages. Stage I uses a relatively narrow channel for particle focusing. Two identical interdigitated transducers (IDTs) are fabricated on a piezoelectric substrate, and a microfluidic channel is aligned between the IDTs. Here the microchannel serves as an acoustic resonator. When the two IDTs are stimulated with RF signals of equal magnitude but 180° out of phase, two series of surface acoustic waves propagate in opposite directions along the surface of the piezoelectric substrate toward the particle solution inside the microchannel. When the surface acoustic wave reaches the medium (i.e., the fluid in the microchannel), leakage waves in longitudinal mode are generated inside the medium, resulting in the pressure fluctuation. The interference of the two acoustic waves forms a standing acoustic wave that generates a periodic distribution of pressure nodes and anti-nodes in the microchannel. Because metal particles have positive acoustic contrast factors ($\phi$), the acoustic radiation forces caused by the pressure fluctuations move the particles toward the pressure nodes in the SSAW field. In Stage I, the width of the microchannel (W1) is chosen to be the half-wavelength ($\lambda\frac{1}{2}$) of the SSAW so that the channel contains only one pressure node located in the center of the channel (FIG. 4.6). Thus, metal particles will aggregate at the centerline of the microchannel. A relatively high power density and a small acoustic wavelength will be used to generate strong acoustic radiation forces, allowing all metal particles to aggregate along the center line by the time they reach the end of the Stage I microchannel. In Stage 2, a wide channel is used; the width of the microchannel (W2) is one-wavelength of the SSAW ($\lambda$2), so that two pressure nodes exist in the channel. Suspended metal particles enter the Stage 2 channel at the anti-node. Thus the acoustic forces will move particles towards the pressure nodes. Because the acoustic force on a particle is proportional to its volume, large particles will move to the pressure-nodes more quickly than small particles. Therefore the particles can be separated by size. Because the flow in microfluidic channels is laminar, the particles will remain in their lateral positions even after they exit the acoustic field. At the end of the SSAW separator, the microchannel will be split into sub-channels to collect and guide separated particles to corresponding inductive Coulter counting detection sensors. The proposed SSAW particle separator is ideal for a metal debris sensor because 1) it is applicable to all types of metal particles regardless of their size, shape, and electrical/magnetic/optical properties, 2) it is a non-invasive method and requires low power intensity [76], and, most importantly, 3) it allows the use of a relatively large microfluidic channel, which will allow for high throughput and cause less problems with clogging.

Develop a Multiplexed Detection Array Utilizing Inductive Coulter Counting Principle Demonstrate Inductive Coulter Counting Principle Because it is difficult to fabricate three-dimensional microscale solenoids, we propose instead to use microscale planar coils as the basis of our sensing mechanism to detect microscale metal particles in lubrication oil. After the metal particles are separated by size into streams, each stream is sent through its own detection channel, so that the particles in a stream pass through the center of a planar coil (see FIG.

4.7) appropriately sized for the range of particle sizes in that stream one by one. Similar to the detection mechanism for a solenoid, an inductance change is expected in the planar coil when a metal particle moves close to its surface, due to changes in magnetic permeability and eddy current. At an appropriate frequency, a ferrous particle is expected to cause a positive inductance pulse due to permeability change, while an aluminum particle is expected to cause a negative inductance pulse due to the dominance of the eddy current effect. The magnitude and the shape of the pulse are indicative of particle's size and shape, respectively. It is worthwhile to note here that because we measure inductive pulses, changes in flow rate and temperature of the lubrication oil, as well as environmental noise due to parasitic inductance and capacitance, affect only the baseline inductance; thus, the inductive Coulter counting method is appropriate for use in relatively harsh environments. Our preliminary testing proved the feasibility of using a microscale planar coil for microscale metal particle detection. We used a 13-turn planar coil from a PL3225TTE4R7M thin film inductor chip (KOA SPEER Electronics, Inc.) after using sandpaper to remove the protective covering of the coil. The planar coil was immersed in SAE 5W-30 lubrication oil. To mimic particles passing through the planar coil's center in fluid flow through a microchannel, metal particles fixed at the free end of a glass fiber were moved toward the center of the coil along the z direction. The glass by itself caused negligible inductance change in the planar coil. FIG. 4.7: Illustration of a single inductive Coulter counting detector. FIG. 4.8 shows the measurement setup and FIG. 4.9 shows the measured relative inductance change (representing half inductive pulse that would be seen in our proposed device) caused as four different metal particles travel along the z direction; measurements are taken at 2 MHz using an LCR meter. The results indicate that a microscale planar coil is able to detect and differentiate ferrous and non-ferrous microscale particles as small as 100 μm, with a pulse height that is related to particle size. The result also suggests that with smaller microscale planar coils fabricated by micromachining, even smaller metal debris particles could be measured and differentiated. As the first step, we propose to fabricate a single microchannel device with a microscale planar coil to further study the inductive Coulter counting principle.

Establish Signal Multiplexing for Parallel Multichannel Detection

To make the particle detection fast enough for real time monitoring, we propose a device with parallel detector array to improve throughput. The improvement in throughput is proportional to the number of the sensing channels n. However, if there are a large number of channels, say on the order of one hundred, it becomes impractical to monitor the measurement pulses of each channel individually. We propose to investigate the use of multiplexing techniques for multichannel measurement. FIG. 4.11 illustrates a simple multiplexing concept in which the set of outputs from the inductive detectors is combined into a single signal. The combined signal would be transmitted to a digital processor which could then separate the signals and interpret their content. The implementation of a multiplexing scheme involves numerous design choices, which depend in part on the implementation of the instrumentation circuit. One possible design, illustrated in FIGS. 4.10 and 4.11, uses instrumentation circuits for which a change in inductance modulates the frequency of an oscillating output voltage. Demodulation of the FM signals would then produce the voltage pulses representing the passage of wear debris particles through the sensors. To achieve sufficient sensitivity, the demodulator circuits may need to include sophisticated subsystems such as phase-locked loops; however, the designs would have to be sufficiently simple and inexpensive that a large number of them could be fabricated for a small embedded system. In alternative implementations, the demodulation circuitry could be simpler, but might not provide sufficient sensitivity. The main research challenge in designing the instrumentation and multiplexing circuitry is to provide adequate sensitivity while ensuring that the design is practical, given the constraints inherent in integrated circuit implementation. The demodulated pulses representing the particles passing through each separate sensor would be combined on a single digital or analog channel by a multiplexer (Mux). It is envisioned that the multiplexer would include digital hardware or software to store the information about the pulses, to convert the information to a digital format, and to gate the digital information onto a digital communication channel. An alternative multiplexer implementation might make use of frequency division for combining the sensor information on a single analog channel. In any case, the design would have to accommodate the signals from a large number of sensors at a data rate sufficiently high that no useful information will be lost, including information about the timing, sizes, and shapes of the individual pulses, each of which represents a single particle passing through the sensor array.

Develop a Micromachining Process:

The proposed device can include two major components, micromachined separately and bonded together, one for particle separation, and one for particle detection. The use of interdigitated (IDT) microelectrodes to generate a standing surface acoustic wave for particle separation and a planar coil for particle detection significantly simplifies the micromachining process as there is no complex 3-D structure. FIG. 4.12 shows the basic sequence used to fabricate the devices. Steps [a-b] are for the IDT microelectrodes for generating standing surface acoustic waves, and steps [c-i] are for the microfluidic channels and planar detection coils. In steps [a-b], we deposit titanium/gold thin film on a LiNbO$_3$ substrate and present photolithography to fabricate the microelectrodes. In steps [c-i], we first etch microchannels onto a silicon substrate using deep reaction ion etching (step d). Next we fabricate planar micro coils on the other surface of the silicon wafer (step e-g). The fabrication of a planar coil includes three sub-steps, including fabrication of coil turns (e), an insulation layer (f) and a top lead strip to trace the inner contact of the coil out (g). We then deposit and pattern a high-resistivity Ni—Zn ferrite (step h) for enhancing the base inductance. The deposition is done by spraying a reaction solution of $FeCl_2+NiCl_2+ZnCl_2$ and an oxidizing solution of $NaNO_2+CH_3COONH_4+NH_4OH$; a Japanese group [77] recently demonstrated deposition of highly permeable ferrite films at a high deposition rate (>60 nm/minute). The Ni—Zn ferrite film can be patterned by Ar sputtering etching or chlorine-based reactive sputtering etching [78]. $Al_2O_3$ will be used as the masking material; it has been shown appropriate for ferrite-selective etches [78]. Subsequently, we etch inlet lead holes and outlet holes using deep reactive ion etching (step i). Finally, the particle separator component and the detection/microfluidic component will be aligned and bonded together using anodic bonding or adhesive bonding (step j).

References, each of which is incorporated herein by reference:

1. Roylance B. J., Williams J. A., and Dwyer-Joyce R., 2000, Wear debris and associated wear phenomena—fundamen- 1. tal research and practice, *Proc. Inst. Mech. Eng.: Part J, J. Eng. Tribolology*, 214, pp. 79-105.
2. Rao B. K. N., 1996, Handbook of Condition Monitoring, Elsevier Advanced Technology, UK.
3. Tucker J. E., Galie T. R., Schultz A., Lu C., Tankersley L. L., Sebok T., Holloway C. and Howard P. L., 2000, LASERNET fines optical wear debris monitor: a Navy shipboard evaluation of CBM enabling technology, *Proc. 54th Meeting of the Society for Machinery Failure Prevention Technology*, pp. 191-199.
4. Saba C., 1990, Improving the wear metal detection of spectrometric oil analysis, *Trans. STLE*, 46, pp. 310-317.
5. Lukas M.; Anderson D., 1991, Techniques to improve the ability of spectroscopy to detect large wear particles in lubricating oils, *Proc. Of International Conference on Condition Monitoring*, Stadthalle, Germany, May 1991.
6. Januszkiewicz K., Sulek H., 1992, UV-Fluorescence Spectroscopic method for monitoring tramp oil contamination in hot rolling emulsions—part II, *Trans. STLE*, 48, pp. 56-61.
7. Bierlein J. A., 1980, Particle-size analysis of engine oils, a supplement to spectrometric analysis, Air Force Materials Laboratory, Technical Report-79-4215, 1980, AD A082230.
8. Kauffman R., 1989, Particle size and composition analysis of wear debris using atomic emission spectrometry, *Trans. STLE*, 45, pp. 147-153.
9. Bartik I., 1986, Filtration: A complex process whose methods are constantly improving, *Canadian Lubrication Journal*, 6, pp. 11-19, 1986.
10. Leugner L. 1987, Use of sediment tests and wear metal analysis to monitor hydraulic system conditions, *ASLE Trans.*, 43, pp. 365-369.
11. Eleftherakis J., Shelton D., Long R., 1995, Accurate assessment of particle counts in liquids, *Trans. STLE*, 51, pp. 205-208.
12. Reintles J., Mahon R., Duncan M. D., Tankersley L. L., Schultz A., Chen V. C., Kover D. J., Howard P. L., Chamberlain M, Raghavan S., Gupta N., 1995, Optical Debris Monitoring, *Proceedings of the 49th Meeting of the Society for Machinery Failure Prevention Technology*, pp. 263-272.
13. Gupta N., Srinivasan S., Raghavan S., Reintjes J., Chen V., Shultz A., 1995, High speed image processing for wear debris monitoring, *Proceedings of the 49th Meeting of the Society for Machinery Failure Prevention Technology*, pp. 273-292.
14. "LASERNET optical oil debris sensor" Navy Research Laboratory—available at http://www.lasernet.com/products_laserxpress.htm.
15. Van de Hulst D. E, 1981, Light scattering by small particles, Wiley Press, New York.
16. Glavas K. E., and Jones G. R., 1993, A fiber optical oil condition monitor based on chromatic modulation, *Meas. Sci. Technology*, 4, pp. 608-613.
17. Pleper K., Taylor I. J., 1988, In-line wear monitoring, AFWAL-TR-88-2095, AD-A201292.
18. Martin S. J., Ricco A. J., Niemczyk T. M. and Frye G. C., 1989, Characterization of the Shear Impedance of SH Acoustic Plate Mode Liquid Sensors, *Sensors and Actuators*, 20, pp. 253-268.
19. Hager H. E., 1986, Fluid Properties Evaluation by Piezoelectric Crystals Operating in Thickness Shear Mode, *Chem. Eng. Commun.*, 43, pp. 25-38.
20. Liu Y., Liu Z., Xie Y., Yao Z., 2000, Research on an on-line wear condition monitoring system for marine diesel engine, *Tribology International*, 33, pp. 829-835.1
21. Keller M., Saba C., 1989, Monitoring of Ester based lubricant by dielectric constant, *Trans. STLE*, 45, pp. 347.
22. Flanagan M., Jordan J. R., and Whittington H. W., 1990, An inductive method for estimating the composition and size of metal particle, *Meas. Sci. Technol.*, 1, pp. 381-394.
23. Flynn B. W., Whittington H. W., 1995, Improved transducer design for machine wear debris monitoring, *Electronic Letters*, 31, pp. 177-179.
24. MetalSCAN User's Manual—Early Failure Detection for Rotating Equipment, GASTOPS Inc., 2002.
25. Dickert A. D., Johnson E. L., Kirkpatrick J. F., Hawn K. A., 1993, Oil monitor with magnetic field, U.S. Pat. No. 5,262,732.
26. Quantitative Debris Monitoring, available at http://www.tedecoindustrial.com/qdm.htm.
27. Campbell P., 1991, On-line monitoring of ferromagnetic debris concentration, *International condition monitoring conference Proceedings*, pp. 325-335.
28. Henriquez R. R., Ito T., Sun L., and Crooks R. M., 2004, The resurgence of Coulter counting for analyzing nanoscale objects, *Analyst*, 6, pp. 478-482.
29. Zhang Z., Zhe J., Chandra S., and Hu J., 2005, An electronic pollen detection method using Coulter counting principle, *Atmospheric Environment*, 39, 30, pp. 5446-5453.
30. Jagtiani A., Sawant R., Zhe J., 2006, A label-free high throughput resistive-pulse sensor for simultaneous differentiation and measurement of multiple particle-laden analytes, *Journal of Micromechanics and. Microengineering*, 16, pp. 1530-1539.
31. Murali S., Xia G., Jagtiani A., J. Carletta and Zhe, J., 2009, Capacitive coulter counting: detection of metal wear particles in lubricant using a microfluidic device, *Smart Materials and Structures*, 18, pp. 03700.
32. Murali S., Jagtiani A., Xia G., Carletta J. and Zhe J., 2009, A Microfluidic Coulter Counting Device for Metal Wear Detection in Lubrication Oil, *Review of Scientific Instruments*, 80, pp. 016105.
33. Du L., Carletta J., Veilette, R. and Zhe J., 2009, A magnetic coulter counting device for wear debris detection in lubrication oil, accepted by *ASME IMECE 2009 Proceedings*, Nov. 13-18, 2009. Lake Buena Vista, Fla.
34. Macdonald M. P., Spalding G. C. and Dholakia K., 2003, Microfluidic sorting in an optical lattice, *Nature*, 426, (6965), pp. 421-424.
35. Macdonald M. P., Neale S, and Paterson L., 2004, Cell cytometry with a light touch: sorting microscopic matter with an optical lattice, *J. Biol. Regul. Homeost. Agents*, 18, pp. 200-205.
36. Smith R. L., Spalding A. G. and. Dholakia A. K, 2007, Colloidal sorting in dynamic optical lattices, *Journal of Optics A*, 9, pp. 134-138.
37. Ladavac K., Kasza K., and Grier D. G., 2004, Sorting mesoscopic objects with periodic potential landscapes: Optical fractionation, *Physical Review E*, 70, pp. 010901.
38. Kim S. B., Yoon S. Y., Sung H. J. and Kim S. S., 2008, Cross-type optical particle separation in a microchannel, *Analytical Chemistry*, 80, pp. 2628-2630.
39. Huang L. R., Cox E. C., Austin R. H., et al., 2004, Continuous particle separation through deterministic lateral displacement, *Science*, 304, pp. 987-990.
40. Davis J. A., Inglis D. W., Morton K. J., et al., 2006, Deterministic hydrodynamics: taking blood apart, *Proceedings of the National Academy of Sciences USA*, 103, pp. 14779-14784.2

41. Bowden S. A., Monaghan P. B., Wilson R., et al., 2006, The liquid-liquid diffusive extraction of hydrocarbons from a North Sea oil using a microfluidic format, *Lab on a Chip*, 6, pp. 740-743.
42. Baldessari F. and Santiago J. G., 2006, Electrophoresis in nanochannels: brief review and speculation, *Journal of Nanobiotechnology*, 4, pp. 189-195.
43. Choi S, and Park J. K., 2005, Microfluidic system for dielectrophoretic separation based on a trapezoidal electrode array, *Lab on a Chip*, 5, pp. 1161-1167.
44. Hu X. Y., Bessette P. H., Qian J. R., et al., 2005, "Marker-specific sorting of rare cells using dielectrophoresis, *Proceedings of the National Academy of Sciences USA*, 102, pp. 15757-15761.
45. Mcgloin D., 2006, Optical tweezers: 20 years on, *Philosophical Transactions of the Royal Society A*, 364, pp. 3521-3537.
46. Libal A., Reichhardt C., Janko B., et al., 2006, Dynamics, rectification, and fractionation for colloids on flashing substrates, *Physics Review Letters*, 96, pp. 188301.
47. Chang-hasnain C. J., 2000, Tunable VCSEL, *IEEE Journal of Selected Topics in Quantum Electronics*, 6, pp. 978-987.
48. Fu A. Y., Spence C., Scherer A., Arnold F. H. and Quake S. R., 1999, "A microfabricated fluorescence-activated cell sorter", *Nature Biotechnology*, 17, pp. 1109-1111.
49. Becker S., Schmoldt H. U., Adams T. M., Wilhelm S. and Kolmar H., 2004, Ultra-highthroughput screening based on cell-surface display and fluorescence-activated cell sorting for the identification of novel biocatalysts, *Current Opinion in Biotechnology*, 15, pp. 323-329.
50. Yamada M., Nakashima M. and Seki M., 2004, Pinched flow fractionation: continuous size separation of particles utilizing a laminar flow profile in a pinched microchannel, *Analytical Chemistry*, 76 (18), pp. 5465-5471.
51. Yamada M. and Seki M., 2005, Hydrodynamic filtration for on-chip particle concentration and classification utilizing microfluidics, *Lab on a Chip*, 5, pp. 1233-1239.
52. Yang S., Undar A., Zahn J. D., 2006, A microfluidic device for continuous, real time blood plasma separation, *Lab on a Chip*, 6, pp. 871-880.
53. Morton K. J., Loutherback K., Inglis D. W., et al., 2008, Hydrodynamic metamaterials: Microfabricated arrays to steer, refract, and focus streams of biomaterials, *Proceedings of the National Academy of Sciences USA*, 105, pp. 7434-7438.
54. Inglis D. W., Davis J. A., Austin R. H. and Sturm J. C., 2006, Critical particle size for fractionation by deterministic lateral displacement, *Lab on a Chip*, 6, pp. 655-658.
55. Inglis D. W., 2009, Efficient microfluidic particle separation arrays, *Applied Physics Letters*, 94, pp. 013510.
56. Kersaudy-Kerhoas M., Dhariwal R. and Desmulliez M. P., 2007, Recent advances in microparticle continuous separation, *IET Nanobiotechnology*, 2, pp. 1-13.
57. Todd P., Sengupta S., Doyle J. F., Vellinger J. and Deuser M. S., 2000, Multistage electrophoresis system for the separation of cells, particles and solutes, *Electrophoresis*, 21, pp. 318-324.
58. Araki T. and Tanaka H., 2008, Physical principle for optimizing electrophoretic separation of charged particles", *A Letter J. Exploring the Frontier of Physics (EPL Journal)*, 82, pp. 18004.
59. Kralj J. G., L is M. T., Schmidt M. A. and Jensen K. F., 2006, Continuous dielectrophoretic size-based particle sorting, *Analytical Chemistry.*, 78, pp. 5019-5025.3
60. Doh I. and Cho Y. H., 2005, Continuous cell separation chip using hydrodynamic dielectrophoresis process, *Sensors Actuators A*, 121, pp. 59-65.
61. Nieuwenhuis J. H., Jachimowicz A., Svasek P., et al., 2005, Optimization of microfluidic particle sorters based on dielectrophoresis, *IEEE Sensors J.*, 5, pp. 810-816.
62. Han K. H. and Frazier A. B., 2008, Lateral-driven continuous dielectrophoretic microseparators for blood cells suspended in a highly conductive medium, *Lab on a Chip*, 8, pp. 1079-1086.
63. Hughes M. P., 2002, Strategies for dielectrophoretic separation in laboratory-on-a-chip systems, *Electrophoresis*, 23, pp. 2569-2582.
64. Velev 0. D. and Bhatt K. H., 2006, On-chip micromanipulation and assembly of colloidal particles by electric fields, *Soft Matter*, 2, pp. 738-750.
65. Hermanson K. D., Lumsdon S. O., Williams J. P., et al., 2001, Dielectrophoretic assembly of electrically functional microwires from nanoparticle suspensions, *Science*, 294, pp. 1082-1086.
66. Morgan H., lzquierdo A. G., Bakewell D. J., Green N. G. and Ramos A., 2001, The dielectrophoretic and traveling wave forces for interdigitated electrode array: analytical solution using fourier series, *J. Physics D: Applied Physics*, 34, pp. 1553-1561
67. Shi J., Mao X., Ahmed D., Colletti A., and Huang T. J., 2008, Focusing microparticles in a microfluidic channel with standing surface acoustic waves, *Lab on a Chip*, 8, pp. 221-223.
68. Kapishnikov S., Kantsler V. and Steinverg V., 2006, Continuous particle size separation and size sorting using ultrasound in a microchannel, *J. Statistical Mechanics: Theory and Experiment*, 1, pp. 01012/(1-15).
69. Nilsson A., Petersson F., Jonsson H., et al., 2004, Acoustic control of suspended particles in micro fluidic chips, *Lab on a Chip*, 4, pp. 131-135.
70. Wiklund M., Gunther C., Lemor R., et al., 2006, Ultrasonic standing wave manipulation technology integrated into a dielectrophoretic chip", *Lab on a Chip*, 6, pp. 1537-1544.
71. Laurell T., Petersson F. and Nilsson A., 2007, Chip integrated strategies for acoustic separation and manipulation of cells and particles, *Chemical Society Reviews*, 36, pp. 492-506.
72. Petersson F., Aberg L. and Laurell T., 2007, Free Flow Acoustophoresis: Mircofliudic-based mode of particle and cell separation, *Analytical Chemistry*, 79, pp. 5117-5123.
73. Nilsson A., Holm C., Jonsson H. and Laurell T., 2004, Separation of lipids from blood utilizing ultrasonic standing waves in microfludic channels, *Analyst*, 129, pp. 938-943.
74. Li H. and Kenny T., 2004, High speed particles separation using ultrasound for micro-TAS and lab-on-a-chip application, *Proc. 26th Ann. Int. Conf. IEEE Eng. Medic. Bio. Soc.*, pp. 2631-2634.
75. Masudo T. and Okada T., 2001, Particle characterization and separation by a coupled acoustic-gravity field, *Analytical Chemistry*, 73, pp. 3467-3471.
76. Shi J., Ahmed D., Mao X., Lin S. S., et al., 2009, Acoustic tweezers: pattering cells and microparticles using standing surface acoustic waves, *Lab on a Chip*, DOI: 10.1039/b910595f.
77. Matsushita, N., Nakamura T, and Masanori A. B. E., 2001, high rate deposition (>60 nm/min) of highly permeable ni-zn ferrite films from aqueous solutions, *Proc. 8th Inter. Conf. on Ferrites*, pp. 503-505.

78. Heijman, M. G. J., 1998, Reactive Sputter Etching of Magnetic Materials in an HCl Plasma, *Plasma Chemistry and Plasma Processing*, 8, (4), pp. 383-397.4

79. Lam, P., Zhao, J., Doverspike, D., Zhe, J., and Menzemer, C., 2008, An Evaluation of a STEM Program for Middle School Students on Learning Disability Related IEPs, *Journal of SMET: Innovations and Research*, 9, (1), pp. 21-29.

80. Zhe, J., Dennis Doverspike, D., Zhao, J., Lam, P. and Menzemer, C., High School Bridge Program: A Multidisciplinary STEM Research Program, accepted by *Journal of STEM Education: Innovations and Research*, 2009.

81. Zhe J., Jagtiani A., Dutta P., Hu J., and Carletta J., 2007, A micromachined high throughput Coulter counter for bioparticle detection and counting, *Journal of Micromechanics and Microengineering*, 17, pp. 304-313.

82. Vasudev A., Jagtiani A., Du L., and Zhe J., 2009, A low-voltage droplet microgripper for micro-object manipulation, *Journal of Micromechanics and Microengineering*, 19, pp. 075005.

83. Vasudev A. and Zhe J., 2008, A Capillary Microgripper based on electrowetting, *Applied Physics Letters*, 93, pp. 103503.

84. Wang Y., Zhe J., Chung B. T., and Dutta P., 2008, A Rapid Magnetic Particle Driven Micromixer, *Journal Microfluidics and Nanofluidics*, 4, pp. 375-389.

85. Duran H., Meng S., Kim N., Hu J., Kyu T., Natarajan. L. V., Tondiglia V. P., and Bunning T. J., 2008, Kinetics of photopolymerization-induced phase separation and morphology development in mixtures of a nematic liquid crystal and multifunctional acrylate, *POLYMER*, 49, pp. 534.

86. Jagtiani A. V., Sawant R., Carletta J. and Zhe J., 2008, Wavelet transform-based methods for denoising of Coulter counter, *Measurement, Science and Technology*, 19, pp. 065102.

87. Ouyang H., Xia Z. H., and Zhe J., 2009, Static and dynamic responses of polyelectrolyte brushes under external electric field, *Nanotechnology*, 20, pp. 195703.

88. Jagtiani A., Carletta J., Hu, J., and Zhe J., 2008, Amplitude Modulated Micro Coulter Counter for High Speed Counting of Microparticles, *Proceedings of 51st IEEE International Midwest Symposium on Circuits and Systems (MWSCAS 2008)*, Aug. 10-13, 2008, in Knoxville, Tenn.

89. Jagtiani A., Carletta J., Hu J., Zhe J., 2008, A High Throughput Multiplexed Micro Coulter Counter Using Amplitude Modulation, *Proceedings of 17th Biennial IEEE UGIM (University Government Industry Micro/nano) Symposium*, Jul. 13-16, 2008, Louisville, Ky.

90. Zhe J., Jagtiani A., Dutta, P., Hu, J. and Carletta, J., A Micromachined High Throughput Bioparticle Sensor, 2007, *Proceedings of the 14th International Conference on Solid State Sensors, Actuators and Microsystems*, June 10-14, Lyon, France, Vol. 2, pp. 1825-1828.

91. Hu J., Zhe J. and Ma Y., Persistent Self-Assembled Monolayers for Micro/Nano Electro-Mechanical Device Fabrications, 2008, *Proceedings of American Chemical Society 40$^{th}$ Central Regional Meeting*, June 10-14, Columbus, Ohio.

92. Vasudev A. and Zhe J., 2008, A Droplet Soft Microgripper Using Electrowetting, *ASME IMECE 2008 Proceedings*, November 2-6, Boston, Mass.

93. Murali S., Gao X., Carletta J. and Zhe, J., 2008, A Microfluidic Sensor for Metal Wear Detection in Lubricants, *ASME IMECE 2008 Proceedings*, November 2-6, Boston, Mass.

94. Vasudev A. and Zhe J., 2009, A Low Voltage Microgripper Using Electrowetting, *Proceedings of IEEE 15th International Conference on Solid-State Sensors, actuators and Microsystems (Transducers'09)*, June 21-25, Denver, Colo., Vol. 1, pp. 825-828.56

95. Weingart J J. and Hu J., 2008, Synthesis and characterization of mixed monolayer protected gold nanoparticles as functional mimics of small cellular vesicles, *Proceedings of 235th ACS National Meeting*, April 6-10, New Orleans, La.

96. Hu J. and Zhe J., 2008, Coulter Counter Having a Plurality of Channels, U.S. Pat. No. 7,397,232, issued July 2008.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the measurement technique and the type of numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A method of separating particles, comprising:
   flowing a plurality of particles, using one singular flow, into a first portion of a single microfluidic channel, wherein the flow is a non-sheath flow,
   focusing the particles to a first area of the first channel using an interference of a first pair of surface acoustic waves,
   flowing the plurality of particles along the first area into a second portion of the single microfluidic channel, wherein the second portion is in fluidic communication with the first channel, and
   separating the plurality of particles along a length of the second portion using an interference of a second pair of surface acoustic waves, wherein separating includes separating the plurality of particles based on the volume, density, and compressibility of the particles as the particles travel the length of the second portion of the single microfluidic channel.

2. The method of claim 1, wherein the first area is at a center area of the first portion of the single microfluidic channel.

3. The method of claim 1, further generating a first pair of surface acoustic waves using a first pair of surface acoustic wave generators positioned on opposite sides of the first portion of the single microfluidic channel, wherein the first pair of surface acoustic waves interfere with one another to form a periodic distribution of one or more pressure nodes and anti-nodes on the first portion of the single microfluidic channel.

4. The method of claim 1, wherein the first pair of surface acoustic wave generators produce a single pressure node.

5. The method of claim 1, wherein first portion of the single microfluidic channel is interfaced with the second portion of the single microfluidic channel so that the center area of the first portion of the single microfluidic channel is ata center area of the second portion of the single microfluidic channel.

6. The method of claim 1, further generating a second pair of surface acoustic waves using a second pair of surface acoustic wave generators positioned on opposite sides of the second portion of the single microfluidic channel, wherein the second pair of surface acoustic waves interfere with one another to form a periodic distribution of one or more pressure nodes and anti-nodes on the second portion of the single microfluidic channel.

7. The method of claim 1, wherein the interference of the surface acoustic waves generated by the second pair of surface acoustic wave generators produce two pressure nodes.

* * * * *